(12) United States Patent
Tinger et al.

(10) Patent No.: US 12,358,857 B2
(45) Date of Patent: Jul. 15, 2025

(54) PROCESSES FOR PRODUCING HIGH-OCTANE-NUMBER FUEL COMPONENT

(71) Applicant: ExxonMobil Chemical Patents Inc., Baytown, TX (US)

(72) Inventors: Robert G. Tinger, Friendswood, TX (US); Theophile E. Foyen, Seabrook, TX (US); Stephen J. Mokulis, Houston, TX (US); Todd E. Detjen, Bellaire, TX (US)

(73) Assignee: ExxonMobil Chemicals Patents Inc., Baytown, TX (US)

( * ) Notice: Subject to any disclaimer, the term of this patent is extended or adjusted under 35 U.S.C. 154(b) by 94 days.

(21) Appl. No.: 18/004,123

(22) PCT Filed: Jul. 6, 2021

(86) PCT No.: PCT/US2021/040453
§ 371 (c)(1),
(2) Date: Jan. 3, 2023

(87) PCT Pub. No.: WO2022/026129
PCT Pub. Date: Feb. 3, 2022

(65) Prior Publication Data
US 2023/0257329 A1    Aug. 17, 2023

Related U.S. Application Data

(60) Provisional application No. 63/059,483, filed on Jul. 31, 2020.

(51) Int. Cl.
C07C 15/08    (2006.01)
C10L 1/04     (2006.01)
C10L 10/10    (2006.01)

(52) U.S. Cl.
CPC ............... C07C 15/08 (2013.01); C10L 1/04 (2013.01); C10L 10/10 (2013.01); *C10L 2200/0423* (2013.01)

(58) Field of Classification Search
CPC . C07C 15/08; C10L 1/04; C10L 10/10; C10L 2200/0423; C10L 2270/023;
(Continued)

(56) References Cited

U.S. PATENT DOCUMENTS

| | | | |
|---|---|---|---|
| 2,683,763 A | 7/1954 | Lien et al. | |
| 3,686,342 A | 8/1972 | Neuzil | |

(Continued)

FOREIGN PATENT DOCUMENTS

| | | |
|---|---|---|
| WO | 2008/036913 A2 | 3/2008 |
| WO | 2013/013492 A1 | 1/2013 |

(Continued)

OTHER PUBLICATIONS

A chemical embrace from the perfect host, ChemEurope.com, King Abdullah University of Science and Technology (KAUST), Retrieved from Internet URL:<https://www.chemeurope.com/en/news/1165640/a-chemical-embrace-from-the-perfect-host.html>, 2020, 2 Pages.

(Continued)

*Primary Examiner* — Ali Z Fadhel
(74) *Attorney, Agent, or Firm* — ExxonMobil Technology and Engineering Company

(57) ABSTRACT

Processes for producing high-octane-number fuel components, particularly those useful for AvGas blends, can be advantageously produced from hydrocarbon feed streams comprising C8+ aromatic hydrocarbons. Such feed streams may be produced by, among others, separation and other optional post-processing of an effluent produced from a steam cracker (e.g., a liquid feed steam cracker cracking liquid feeds such as naphtha and/or other crude fractions, a (Continued)

gas steam cracker cracking gas feeds such as ethane and/or propane), hydrocarbon reforming of a crude fraction or steam cracker effluent fraction, C6-C7 aromatic hydrocarbon methylation, transalkylation between C6-C7 aromatic hydrocarbons and C9+ aromatic hydrocarbons, isomerization of C8 aromatic hydrocarbons, and toluene disproportionation processes.

24 Claims, 1 Drawing Sheet

(58) Field of Classification Search
CPC .... C10L 2290/542; C10L 1/06; C10L 1/1616; C10G 2300/1037; C10G 2400/30; C10G 7/00
See application file for complete search history.

(56) References Cited

U.S. PATENT DOCUMENTS

| | | | |
|---|---|---|---|
| 4,571,444 | A | 2/1986 | Black et al. |
| 4,613,725 | A | 9/1986 | Barthomeuf |
| 4,886,929 | A | 12/1989 | Neuzil et al. |
| 5,752,990 | A | 5/1998 | Siskin et al. |
| 5,849,981 | A | 12/1998 | Kulprathipanja |
| 5,939,597 | A | 8/1999 | Dessau et al. |
| 5,977,420 | A | 11/1999 | Abichandani et al. |
| 6,180,008 | B1 | 1/2001 | White |
| 6,187,987 | B1 | 2/2001 | Chin et al. |
| 6,423,879 | B1 | 7/2002 | Brown et al. |
| 6,486,373 | B1 | 11/2002 | Abichandani et al. |
| 6,504,072 | B1 | 1/2003 | Brown et al. |
| 6,642,426 | B1 | 11/2003 | Johnson et al. |
| 7,074,739 | B2 | 7/2006 | Dakka et al. |
| 7,176,339 | B2 | 2/2007 | Iaccino et al. |
| 7,276,638 | B2 | 10/2007 | Dakka et al. |
| 7,326,818 | B2 | 2/2008 | Beeckman et al. |
| 7,396,967 | B2 | 7/2008 | Iaccino et al. |
| 7,453,018 | B2 | 11/2008 | Dakka et al. |
| 7,655,823 | B2 | 2/2010 | Mohr et al. |
| 7,663,010 | B2 | 2/2010 | Levin |
| 7,740,668 | B2 | 6/2010 | Gaughan et al. |
| 7,799,962 | B2 | 9/2010 | Dakka et al. |
| 7,902,414 | B2 | 3/2011 | Ou et al. |
| 8,183,424 | B2 | 5/2012 | Levin et al. |
| 8,344,197 | B2 | 1/2013 | Lattner et al. |
| 8,628,594 | B1 * | 1/2014 | Braly ................ C10L 1/06 44/426 |
| 8,835,705 | B2 | 9/2014 | Cao et al. |
| 8,940,950 | B2 | 1/2015 | Ellrich et al. |
| 9,095,831 | B2 | 8/2015 | Han et al. |
| 9,440,893 | B2 | 9/2016 | Helton et al. |
| 10,260,016 | B2 | 4/2019 | Braly |
| 10,550,347 | B2 | 2/2020 | Braly |
| 10,661,258 | B2 | 5/2020 | Detjen et al. |
| 2009/0069612 | A1 | 3/2009 | Hotier et al. |
| 2011/0319688 | A1 | 12/2011 | Ou |
| 2012/0108867 | A1 * | 5/2012 | Pilliod ................ C07C 7/04 585/300 |
| 2012/0108868 | A1 | 5/2012 | Pilllod et al. |
| 2013/0274532 | A1 | 10/2013 | Porter |
| 2014/0023563 | A1 | 1/2014 | Ou |
| 2015/0051430 | A1 | 2/2015 | Ou et al. |
| 2015/0299071 | A1 | 10/2015 | Ou et al. |
| 2017/0081259 | A1 | 3/2017 | Molinier et al. |
| 2017/0247303 | A1 | 8/2017 | Thirasak et al. |
| 2019/0225900 | A1 | 7/2019 | Braly |

FOREIGN PATENT DOCUMENTS

| | | |
|---|---|---|
| WO | 2013/013493 A1 | 1/2013 |
| WO | 2015/047680 A1 | 4/2015 |
| WO | 2022/026129 A1 | 2/2022 |

OTHER PUBLICATIONS

U.S. Appl. No. 62/876,391, "Processes for Converting Aromatic Hydrocarbons via Alkyl-Demethylation", filed Jul. 19, 2019, 76 Pages.
International Preliminary Report on Patentability received for PCT Application No. PCT/US2021/040453, mailed on Feb. 9, 2023, 14 Pages.
International Search Report and Written Opinion received for PCT Application No. PCT/US2021/040453, mailed on Dec. 1, 2021, 20 Pages.
Invitation to Pay Additional Fees and, Where Applicable, Protest Fee received for PCT Application No. PCT/US2021/040453, mailed on Oct. 6, 2021, 12 Pages.
Zhang, F. et al., "Selective Separation of Toluene/n-Heptane by Supported Ionic Liquid Membranes with [Bmim] [BF4]", Chemical Engineering & Technology, vol. 38, No. 2, 2015, pp. 355-361.

* cited by examiner

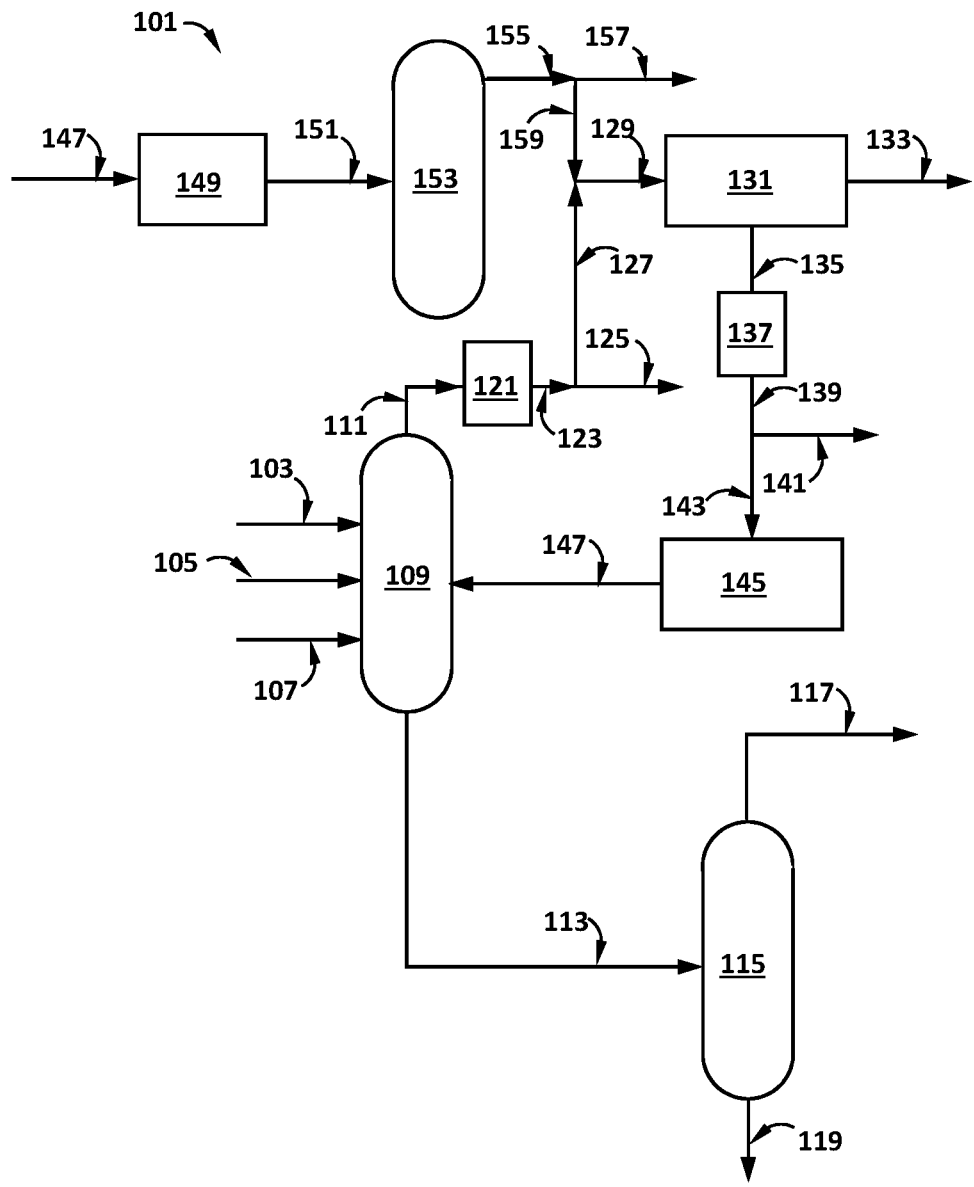

PROCESSES FOR PRODUCING HIGH-OCTANE-NUMBER FUEL COMPONENT

CROSS-REFERENCE TO RELATED APPLICATIONS

This application is a U.S. national phase application of PCT Application Serial No. PCT/US2021/040453 having a filing date of Jul. 6, 2021, which claims priority to and the benefit of U.S. Provisional Application No. 63/059,483 having a filing date of Jul. 31, 2020, the disclosures of both of which are incorporated herein by reference in their entireties.

FIELD

This disclosure relates to motor fuels, components for motor fuels, and processes for producing such components. In particular, this disclosure relates to lead-free aviation gasolines, high-octane hydrocarbon components for lead-free aviation gasolines, and processes for producing such hydrocarbon components.

BACKGROUND

In the combustion chambers of internal combustion engines, such as the engines propelling certain airborne vehicles, typically a hydrocarbon-based fuel (e.g., gasolines and diesels) combusts optionally upon initiation by a spark generated by a spark plug, to produce the mechanical energy output. Stable, controlled combustion of the fuel necessitates the fuel to have a certain minimal motor octane number to prevent undesirable explosion causing engine knocking. Certain additives such as tetraethyl lead have been used to boost the overall octane number of the fuel. It is highly desirable to reduce or eliminate tetraethyl lead from fuel compositions for environmental and health reasons.

U.S. Pat. Nos. 8,628,594, 10,260,016, 10,550,347, and U.S. Patent Application Publication No. 2019/0225900 A1 disclose various lead-free aviation gasoline ("AvGas") formulations comprising high octane-number aromatic hydrocarbons such as trimethylbenzenes, xylenes, and mixtures thereof, the relevant contents of which are incorporated herein by reference. U.S. Pat. Nos. 5,752,990 and 7,740,668 further disclose various lead-free AvGas formulations comprising various non-lead additives, the relevant contents of which are incorporated herein by reference.

There is a continued need for high-octane-number fuel component, particularly AvGas component, and particularly processes for making them. This disclosure satisfies this and other needs.

SUMMARY

It has been found that high-octane-number fuel components, particularly those useful for AvGas blends, can be advantageously produced from hydrocarbon feed streams comprising C8+ aromatic hydrocarbons. Such hydrocarbon feed streams can be produced by, among others, processing of biofeeds such as sugars, wood, or re-use materials, processes converting crude to condensate, processes for converting methane to syngas, separation and other optional post-processing of an effluent produced from a steam cracker (e.g., a liquid feed steam cracker cracking liquid feeds such as naphtha and/or other crude fractions, a gas steam cracker cracking gas feeds such as ethane and/or propane), hydrocarbon reforming of a crude fraction or steam cracker effluent fraction, C6-C7 aromatic hydrocarbon methylation, transalkylation between C6-C7 aromatic hydrocarbons and C9+ aromatic hydrocarbons, isomerization of C8 aromatic hydrocarbons, toluene disproportionation processes, and the like. One or more streams in these processes and mixtures thereof may be suitable as high-octane fuel component(s). The processes can be advantageously configured to produce additional products such as p-xylene and o-xylene.

A first aspect of this disclosure relates to a process for producing a high-octane-number fuel component. The process can comprise (I) providing a first C8+ hydrocarbon stream comprising p-xylene, o-xylene, m-xylene, and optionally ethylbenzene. The process can further comprise (II) feeding the first C8+ hydrocarbon stream into a C8 splitter to obtain a first o-xylene-rich stream depleted in p-xylene and m-xylene, and a first o-xylene-depleted stream rich in p-xylene and m-xylene. The process can further comprise (III) optionally feeding the first o-xylene-depleted stream to a p-xylene recovery sub-system, from which a p-xylene product stream rich in p-xylene and a raffinate stream depleted in p-xylene are obtained. The process can further comprise (IV) obtaining the high-octane-number fuel component from one or more of: at least a portion of the first o-xylene-depleted stream; at least a portion of the raffinate stream; and a mixture of at least a portion of the first o-xylene-depleted stream and at least a portion of the raffinate stream.

A second aspect of this disclosure relates to a process for producing a high-octane-number fuel component. The process can comprise (A) feeding toluene into a toluene disproportionation zone. The process can further comprise (B) converting at least a portion of the toluene in the presence of a shape selective catalyst to produce a disproportionation effluent comprising C7, C8, and C9+ aromatic hydrocarbons. The process can further comprise (C) obtaining from the disproportionation effluent a disproportionation C8+ stream consisting essentially of C8+ aromatic hydrocarbons having a p-xylene concentration of at least 50 wt %, based on the total weight of the second disproportionation C8+ stream. The process can further comprise (D) feeding at least a portion of the disproportionation C8+ stream to a p-xylene recovery sub-system, from which a p-xylene product stream rich in p-xylene and a raffinate stream depleted in p-xylene are obtained. The process can further comprise (E) obtaining at least a portion of the high-octane-number fuel component from the raffinate stream.

A third aspect of this disclosure relates to a process for producing a high-octane-number fuel component. The process can comprise (a) feeding C6-C7 aromatic hydrocarbon(s) and a methylating agent into a methylation zone. The process can further comprise (b) reacting the C6-C7 aromatic hydrocarbons with the methylating agent in the methylation zone in the presence of a methylation catalyst under methylation conditions to produce a methylation effluent comprising C7 and C8+ aromatic hydrocarbons. The process can further comprise (c) obtaining from the methylation effluent a methylation C8+ stream consisting essentially of C8+ aromatic hydrocarbons having a p-xylene concentration of at least 25 wt %, based on the total weight of the methylation C8+ stream. The process can further comprise (d) feeding at least a portion of the methylation C8+ stream to a p-xylene recovery sub-system, from which a p-xylene product stream rich in p-xylene and a raffinate stream depleted in p-xylene are obtained. The process can further comprise (e) obtaining at least a portion of the high-octane-number fuel component from the raffinate stream.

A fourth aspect of this disclosure relates to a process for producing a high-octane-number fuel component. The process can comprise (1) providing a C8 aromatic hydrocarbon stream comprising p-xylene, o-xylene, m-xylene, and optionally ethylbenzene. The process can further comprise (2) feeding the C8 aromatic hydrocarbon stream to a p-xylene recovery sub-system, from which a p-xylene product stream rich in p-xylene and a raffinate stream depleted in p-xylene are obtained. The process can further comprise (3) obtaining the high-octane-number fuel component from one or more of: at least a portion of the C8 aromatic hydrocarbon stream; at least a portion of the raffinate stream; and a mixture of at least a portion of the C8 aromatic hydrocarbon stream and at least a portion of the raffinate stream.

BRIEF DESCRIPTION OF THE FIGURE

The FIGURE is a schematic diagram illustrating one or more embodiments of the processes of this disclosure capable of producing one or more hydrocarbon streams suitable as high-octane-number fuel component(s) (particularly high-octane-number AvGas component(s)), an optional p-xylene product, and an optional o-xylene product.

DETAILED DESCRIPTION

1. Definitions

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step(s), or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a distillation column" include embodiments where one, two or more distillation columns are used, unless specified to the contrary or the context clearly indicates that only one distillation column is used. Likewise, "a C9+ stream" should be interpreted to include one, two, or more C9+ components, unless specified or indicated by the context to mean only one specific C9+ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm", as used herein, are ppm by weight unless specified otherwise. All concentrations herein are expressed on the basis of the total amount of the composition in question. Thus, e.g., the concentrations of the various components of a feed composition are expressed based on the total weight of the feed composition. All ranges expressed herein should include both end points as two specific embodiments unless specified or indicated to the contrary.

"Aviation gasoline" or "AvGas" interchangeably means a fuel composition suitable for internal combustion engines of airborne vehicles. Specifications for AvGas are provided in, e.g., ASTM D910 and various government regulations such as those from the Federal Aviation Administration of the United States.

"Hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). The term "Cn aromatic hydrocarbon," where n is a positive integer, means (i) any aromatic hydrocarbon compound comprising carbon atom(s) in its molecule at the total number of n, or (ii) any mixture of two or more such aromatic hydrocarbon compounds in (i). Thus, a C2 hydrocarbon can be ethane, ethylene, acetylene, or mixtures of at least two of them at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cm to Cn aromatic hydrocarbon" or "Cm-Cn hydrocarbon," where m and n are positive integers and m<n, means any of Cm, Cm+1, Cm+2, . . . , Cn−1, Cn aromatic hydrocarbons, or any mixtures of two or more thereof. A "Cn+ hydrocarbon" means (i) any hydrocarbon compound comprising carbon atom(s) in its molecule at the total number of at least n, or (ii) any mixture of two or more such hydrocarbon compounds in (i). A "Cn-hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s). A "Cn+ aromatic hydrocarbon" means (i) any aromatic hydrocarbon compound comprising carbon atom(s) in its molecule at the total number of at least n, or (ii) any mixture of two or more such aromatic hydrocarbon compounds in (i). A "Cn-aromatic hydrocarbon" means (i) any aromatic hydrocarbon compound comprising carbon atoms in its molecule at the total number of at most n, or (ii) any mixture of two or more such aromatic hydrocarbon compounds in (i). A "Cm aromatic hydrocarbon stream" means a hydrocarbon stream consisting essentially of Cm aromatic hydrocarbon(s). A "Cm-Cn aromatic hydrocarbon stream" means a hydrocarbon stream consisting essentially of Cm-Cn aromatic hydrocarbon(s).

An "aromatic hydrocarbon" is a hydrocarbon comprising an aromatic ring in the molecule structure thereof. A "non-aromatic hydrocarbon" means a hydrocarbon other than an aromatic hydrocarbon.

In this disclosure, o-xylene means 1,2-dimethylbenzene, m-xylene means 1,3-dimethylbenzene, and p-xylene means 1,4-dimethylbenzene. The generic term "xylene," either in singular or plural form, shall collectively mean one of or any mixture of two or three of p-xylene, m-xylene, and o-xylene at any proportion thereof.

"Rich" or "enriched" when describing a component in a stream means that the stream comprises the component at a concentration higher than a source material from which the stream is derived. "Depleted" when describing a component in a stream means that the stream comprises the component at a concentration lower than a source material from which the stream is derived. Thus, in embodiments where an admixture stream comprising an aromatic hydrocarbon and a non-aromatic hydrocarbon is separated by a membrane separator comprising a polar membrane to produce a permeate stream comprising the aromatic hydrocarbon at a higher concentration than the admixture stream and the non-aromatic hydrocarbon at a lower concentration than the admixture stream, the permeate stream is rich or enriched in the aromatic hydrocarbon and depleted in the non-aromatic hydrocarbon relative to the admixture stream.

"Consisting essentially of" as used herein means the composition, feed, or effluent comprises a given component at a concentration of at least 60 wt %, preferably at least 70 wt %, more preferably at least 80 wt %, more preferably at least 90 wt %, still more preferably at least 95 wt %, based on the total weight of the composition, feed, or effluent in question.

"Essentially free of" and "substantially free of" as interchangeably used herein mean the composition, feed, or effluent comprises a given component at a concentration of at most 10 wt %, preferably at most 8 wt %, more preferably at most 5 wt %, more preferably at most 3 wt %, still more preferably at most 1 wt %, based on the total weight of the composition, feed, or effluent in question.

In this disclosure, "motor octane number" is determined by ASTM D2700. When used alone herein, "octane" and "octane number" mean motor octane number. Motor octane number is sometimes abbreviated as "MON" herein. A "high octane number" means a MON ≥95, preferably ≥96, more preferably ≥97, more preferably ≥98, more preferably ≥99, still more preferably ≥100. Pure p-xylene, o-xylene, m-xylene, ethylbenzene, and 1,3,5-trimethylbenzene have MONs of about 105, 85-94, 105, 90-102, and 120, respectively. As such, p-xylene, m-xylene, and trimethylbenzenes are more preferable than o-xylene and ethylbenzene as ingredients of a high-octane-number fuel component from the perspective of octane number of the fuel composition formulated from the fuel component, especially if a high octane number of ≥98 is desired for the fuel composition.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6th Edition, by F. Albert Cotton et al. (John Wiley & Sons, Inc., 1999).

2. AvGas

To date, certain aircrafts, such as helicopters, agricultural airplanes for applying pesticides, police patrol airplanes, and the like, are still propelled by internal combustion engines requiring AvGas as fuel. To meet the specification requirements imposed by the governments, it is highly desirable that AvGas are free of tetraethyl lead as an octane number booster. It has been proposed that high octane number aromatic hydrocarbons, such as m-xylene, p-xylene, and 1,3,5-trimethylbenzenes may be included in AvGas at various quantities to improve the overall octane number of an AvGas product. It is also generally desirable that the AvGas have a freezing temperature no higher than −58° C. to ensure adequate performance under low temperature conditions such as during winter and at high altitude.

Preferred AvGas can comprise various base stocks, fuel additives, and a high octane component produced by the processes of this disclosure. Useful base stocks include but are not limited to high quality aviation alkylate, commercial isooctane, or mixtures thereof. Useful additives include but are not limited to: (i) low-boiling point alkyl pyridines, 4-vinylpyridine, DMF, N-formylpiperidine, sulfolane, polyolefin, polyether or polyether amine derivatives of DMF, amidene, or N-substituted-2 pyrrolidones as disclosed in U.S. Pat. No. 5,752,990, and (ii) aromatic amines having the following formula (F-I) as disclosed in U.S. Pat. Nos. 7,740,668 and 8,628,594:

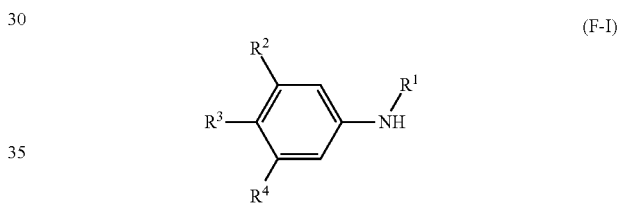

where $R^1$, $R^2$, $R^3$, and $R^4$ can be each independently a C1-C3 alkyl group or hydrogen, provided that at least one of $R^1$, $R^2$, $R^3$, and $R^4$ is not hydrogen. Non-limiting examples of the aromatic amine having formula (F-I) are toluidines (2-methylaniline, 3-methylaniline, 4-methylaniline, and mixtures of two or three thereof).

3. The High Octane Fuel Component Obtainable from the Processes of This Disclosure The high-octane-number fuel component of this disclosure can be used in any motor fuel such as gasoline or diesel for any internal combustion engine. Preferably, the fuel component of this disclosure is used for making AvGas. More preferably, the fuel component of this disclosure is used for making high-octane number, lead-free fuel compositions, such as high-octane-number lead-free AvGas. The fuel component of this disclosure generally comprises C8+ aromatic hydrocarbons. In one preferred embodiment, the fuel component can consist essentially of C8-C11 aromatic hydrocarbons. In another embodiment, the fuel component can consist essentially of C8-C10 aromatic hydrocarbons. In another embodiment, the fuel component can consist essentially of C8-C9 aromatic hydrocarbons. In another embodiment, the fuel component can consist essentially of C8 aromatic hydrocarbons. In still another embodiment, the fuel component can consist essentially of xylenes. In yet a preferred embodiment, the fuel component can consist essentially of m-xylene and/or p-xylene. In yet another preferred embodiment, the fuel component can consist essentially of m-xylene. In yet another preferred embodiment, the fuel component can consist essentially of trimethylbenzenes. The fuel component of this disclosure can comprise non-aromatic hydrocarbons co-boiling with the aromatic hydrocarbons mentioned above at various concentrations.

In various embodiments, the fuel component obtainable from the processes of this disclosure can have one or more of the following features:

(a) an o-xylene concentration from $c(oX)1$ wt % to $c(oX)2$ wt %, based on the total weight of the high octane number fuel component, wherein $c(oX)1$ and $c(oX)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, as long as $c(oX)1<c(oX)2$, preferably $c(oX)2\leq10$; preferably $c(oX)2\leq8$; still more preferably $c(oX)2\leq5$; still more preferably $c(oX)2\leq3$. O-xylene at a high concentration can lead to a low overall octane number of the component;

(b) a p-xylene concentration from $c(pX)1$ wt % to $c(pX)2$ wt %, based on the total weight of the high octane number fuel component, wherein $c(pX)1$ and $c(pX)2$ can be, independently, e.g., 0, 0.1, 0.2, 0.4, 0.5, 0.6, 0.8, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 99, 100, as long as $c(pX)1<c(pX)2$; preferably $c(pX)2\leq95$; preferably $c(pX)2\leq90$; preferably $c(pX)2\leq80$; preferably $c(pX)2\leq70$; preferably $c(pX)2\leq60$; preferably $c(pX)2\leq50$; preferably $c(pX)2\leq40$, as long as $c(pX)1<c(pX)2$; preferably $c(pX)2\leq30$; more preferably $c(pX)2\leq25$; still more preferably $c(pX)2\leq20$; still more preferably $c(pX)2\leq15$; still more preferably $c(pX)2\leq10$. Although a high p-xylene concentration can contribute to a high octane number of the fuel component, it can be detrimental to the freezing point of the fuel composition formulated from the fuel component because of the high melting point of p-xylene (13° C.);

(b) an m-xylene concentration from $c(mX)1$ wt % to $c(mX)2$ wt %, based on the total weight of the high octane number fuel component, wherein $c(mX)1$ and $c(mX)2$ can be, independently, e.g., 0, 0.1, 0.2, 0.4, 0.5, 0.6, 0.8, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 99, 100, as long as $c(mX)1<c(mX)2$; preferably $c(mX)1\geq50$; preferably $c(mX)1\geq60$; preferably $c(mX)1\geq70$; preferably $c(mX)1\geq80$; preferably $c(mX)1\geq90$; preferably $c(mX)1\geq95$. A high concentration of m-xylene in the fuel component of this disclosure is desirable due to its high octane number (105) and a low melting point (−48° C.).

(c) an ethylbenzene concentration from $c(EB)1$ wt % to $c(EB)2$ wt %, based on the total weight of the high octane number fuel component, wherein $c(EB)1$ and $c(EB)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 11, 12, 13, 14, 15, 16, 17, 18, 19, 20, 21, 22, 23, 24, 25, as long as $c(EB)1<c(EB)2$; preferably $c(EB)2\leq20$; more preferably $c(EB)2\leq15$; more preferably $c(EB)2\leq10$; still more preferably $c(EB)2\leq5$. Ethylbenzene at a high concentration can lead to a low overall octane number of the component;

(d) a total non-aromatic hydrocarbon concentration from $c(nA)1$ wt % to $c(nA)2$ wt %, based on the total weight of the high octane number fuel component, wherein $c(nA)1$ and $c(nA)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 15, 20, 25, as long as $c(nA)1<c(nA)2$. Preferably $c(nA)\leq5$; more preferably $c(nA)2\leq3$; and still more preferably $c(nA)2\leq1$. Such non-aromatic hydrocarbons can be, e.g., co-boilers of C8-C11 aromatic hydrocarbons contained in the fuel component. A high total non-aromatic hydrocarbon concentration can lead to a low octane number of the fuel component. In one particularly desirable embodiment, the component is essentially free of linear paraffins, which, if at significant concentration, can lower the octane number of the component significantly; and (e) an octane number ≥95, preferably ≥96, preferably ≥97, preferably ≥98, preferably ≥99, preferably ≥100, preferably ≥101, preferably ≥102, still more preferably ≥103, as determined by ASTM D2700.

4. Processes for Producing Fuel component of This Disclosure 4.1 Processes of the First Aspect of This Disclosure In a first aspect of this disclosure, the process can comprise the following steps:

(I) providing a first C8+ hydrocarbon stream comprising p-xylene, o-xylene, m-xylene, and optionally ethylbenzene;

(II) feeding the first C8+ hydrocarbon stream into a C8 splitter to obtain a first o-xylene-rich stream depleted in p-xylene and m-xylene, and a first o-xylene-depleted stream rich in p-xylene and m-xylene;

(III) optionally feeding the first o-xylene-depleted stream to a p-xylene recovery sub-system, from which a p-xylene product stream rich in p-xylene and a raffinate stream depleted in p-xylene are obtained; and (IV) obtaining the high-octane-number fuel component from one or more of: at least a portion of the first o-xylene-depleted stream; at least a portion of the raffinate stream; and a mixture of at least a portion of the first o-xylene-depleted stream and at least a portion of the raffinate stream.

In various embodiments of the first aspect of this disclosure, the process can further comprise:

(V) feeding at least a portion of the raffinate stream to an isomerization zone operated under isomerization conditions to convert at least a portion of m-xylene in the raffinate stream into p-xylene and/or at least a portion of ethylbenzene, if any, in the raffinate stream into at least one of benzene, toluene, and/or xylenes, to obtain an isomerization effluent stream comprising mixed xylenes; and (VI) obtaining a second C8+ hydrocarbon stream from the isomerization effluent stream; and (VII) feeding the second C8+ hydrocarbon stream or a portion thereof to the C8 splitter.

In various embodiments of the first aspect of this disclosure, the process can further comprise:

(VIII) feeding toluene into a second toluene disproportionation zone;

(IX) converting at least a portion of the toluene in step (VIII) in the presence of a shape selective catalyst to produce a second disproportionation effluent comprising C7, C8, and C9+ aromatic hydrocarbons;

(X) obtaining from the second disproportionation effluent a second disproportionation C8 stream consisting essentially of C8 aromatic hydrocarbons having a p-xylene concentration of at least 25 wt %, based on the total weight of the second disproportionation C8 stream; and (XI) feeding at least a portion of the second disproportionation C8 stream to the p-xylene recovery subsystem of step (III).

In various embodiments of the first aspect of this disclosure, the process can further comprise:

(XII) feeding C6-C7 aromatic hydrocarbon(s) (preferably toluene) and a methylating agent (e.g., methanol, dimethyl ether, and combinations thereof) into a second methylation zone;

(XIII) reacting the C6-C7 aromatic hydrocarbons with the methylating agent in the second methylation zone in the presence of a second methylation catalyst under second methylation conditions to produce a second methylation effluent comprising C7 and C8 aromatic hydrocarbons;

(XIV) obtaining from the second methylation effluent a methylation C8 stream consisting essentially of C8 aromatic hydrocarbons having a p-xylene concentration of at least 25 wt %, based on the total weight of the second methylation C8 stream; and (XV) feeding at least a portion of the second methylation C8 stream to the p-xylene recovery sub-system of step (III).

In various embodiments, the processes of the first aspect of this disclosure can further comprise:

(XVI) separating the first o-xylene-rich stream to obtain an o-xylene product stream and a C9+ hydrocarbon stream; and (XVII) obtaining at least a portion of the high-octane-number fuel component from at least a portion of the C9+ hydrocarbon stream.

Step (I)

In various embodiments of the first aspect, step (I) can comprise:

(I-a) feeding a reformer feed stream comprising paraffins and/or naphthenes into a reformer;

(I-b) converting at least a portion of the paraffins and/or naphthenes into aromatic hydrocarbons in the reformer in the presence of a reforming catalyst under reforming conditions (e.g., a temperature from 427 to 565° C. (800 to 1050° F.), a pressure from 241 to 3,447 kilopascal (gauge) (from 35 to 500 psig), and a liquid hourly space velocity ("LHSV") from 0.3 to 3.0 hour-1) to produce a reformer effluent comprising C6, C7, C8, and C9+ aromatic hydrocarbons;

(I-c) obtaining from the reformer effluent a reformate C8+ stream consisting essentially of C8+ hydrocarbons; and (I-d) obtaining at least a portion of the first C8+ hydrocarbon stream from the reformate C8+ stream.

The reformer feed stream can be derived from, e.g., a crude distillation column, a crude cracker effluent, a stream cracker effluent, a fluid catalytic cracker ("FCC") effluent, and the like, and combinations thereof. Processes and catalysts useful for reforming linear/branched paraffins and naphthenes to produce aromatic hydrocarbons and high octane number liquid products can be found in, e.g., Catalytic Reforming, by Donald M Little, Penn Well Publishing Company (1985), the relevant contents of which are incorporated herein by reference in its entirety. Preferably, in step (I-b), the converting is performed under high severity reforming conditions including a temperature of 527 to 543° C. (980 to 1010° F.), which can result in a low concentration of linear paraffins in and a high octane number of the reformer effluent, and hence the reformate C8+ stream. Step (Ic) can include a step of distilling 6, the reformer effluent to obtain a C7-hydrocarbon stream and a C8+ hydrocarbon stream as the reformate C8+ stream. The reformate C8+ stream, or a portion thereof, can be provided as the first C8 hydrocarbon stream or a portion thereof. Alternatively, the reformate C8+ stream can be further separated in, e.g., a distillation column, to provide a C8 hydrocarbon stream, which is then provided as the first C8+ hydrocarbon stream, or a portion thereof. It is highly desirable that the reformate C8+ stream is essentially free of linear paraffin. To that end, the reformer effluent or a portion thereof may be subjected to a step of solvent-assisted extraction, whereby at least a portion of the paraffins and/or other non-aromatic hydrocarbons is removed to produce the reformate C8+ stream.

In various embodiments, the reformate C8+ stream can comprise ethylbenzene at a concentration from $c(EB)5$ wt % to $c(EB)6$ wt %, based on the total weight of the reformate C8 stream, where $c(EB)5$ and $c(EB)6$ can be, independently, e.g., 0, 0.02, 0.04, 0.05, 0.06, 0.08, 0.1, 0.2, 0.4, 0.5, 0.6, 0.8, 1, 2, 3, 4, 5, 6, 8, 10, 12, 14, 15, 16, 18, 20, 22, 24, 25, 26, 28, 30, as long as $c(EB)5<c(EB)6$.

Where the reformate C8+ stream comprises ethylbenzene at a high concentration, e.g., ≥5 wt %, or ≥8 wt %, or ≥10 wt %, it may be desirable to remove at least a portion of it. In such embodiments, step (I-c) can comprise: (I-c-1) obtaining a C6+ hydrocarbon stream from the reformer effluent; (I-c-2) feeding at least a portion of the C6+ hydrocarbon stream into a second ethylbenzene conversion zone; (I-c-3) converting at least a portion of the ethylbenzene in the C6+ hydrocarbon stream in the second conversion zone in the presence of a second ethylbenzene conversion catalyst into benzene to obtain a second ethylbenzene conversion zone effluent; and (I-c-4) obtaining the reformate C8 stream from the second ethylbenzene conversion zone effluent. Exemplary ethylbenzene conversion catalysts and processes useful for these steps can be found, e.g., in U.S. Pat. No. 5,977,420, the relevant contents of which are incorporated herein by reference.

In certain desirable embodiments, to achieve a relatively low ethylbenzene concentration in the reformate C8+ stream, step (I-d) summarily described above can comprise: (I-d-1) removing at least a portion of the ethylbenzene in the reformate C8 stream to obtain a third C8 stream having a reduced ethylbenzene concentration compared to the reformate C8 stream; and (I-d-2) providing at least a portion of the third C8 stream as the at least a portion of the first C8+ hydrocarbon stream. In preferred embodiments, step (I-d-1) comprises distilling the reformate C8 stream and/or extracting the reformate C8 stream using an extraction solvent to remove the at least a portion of the ethylbenzene in the reformate C8 stream. In other preferred embodiments, step (I-d-1) can comprise: (I-d-1-a) feeding at least a portion of the reformate C8 stream into a first ethylbenzene conversion zone; (I-d-1-b) converting at least a portion of the ethylbenzene in the reformate C8 stream in the first ethylbenzene conversion zone in the presence of a first ethylbenzene conversion catalyst to into benzene to obtain a first ethylbenzene conversion zone effluent; and (I-d-1-c) obtaining the third C8 stream from the first ethylbenzene conversion effluent consisting essentially of xylenes and having an ethylbenzene concentration lower than the reformate C8 stream. Exemplary ethylbenzene conversion catalysts and processes useful for these steps can be found, e.g., in U.S. Pat. No. 5,977,420, the relevant contents of which are incorporated herein by reference.

In various embodiment of the process of the first aspect of this disclosure, at least a portion of the first C8+ aromatic hydrocarbon stream can be obtained from a transalkylation process, In such embodiments, step (I) may comprise the following: (I-e) feeding a C9+ aromatic hydrocarbon stream and a C6-C7 aromatic hydrocarbon stream into a transalkylation zone; (I-f) converting at least a portion of the C9+ aromatic hydrocarbons and C6-C7 aromatic hydrocarbons under transalkylation conditions in the transalkylation zone in the presence of a transalkylation catalyst to produce a transalkylation effluent comprising C6, C7, C8, and C9+ aromatic hydrocarbons; (I-g) obtaining from the transalkylation effluent a transalkylation C8 stream consisting essentially of C8 aromatic hydrocarbons; and (I-h) obtaining at least a portion of the first C8+ hydrocarbon stream from the transalkylation C8 stream. The transalkylation effluent, and hence the transalkylation C8 stream, can advantageously comprise ethylbenzene a low concentration (even if the C9+ aromatic hydrocarbons comprise substantial quantity of ethyl and/or propyl-substituted aromatic hydrocarbons), making it particularly suitable as the first C8+ hydrocarbon stream or a portion thereof. Exemplary transalkylation zone, transalkylation catalyst, and transalkylation conditions can be found in, e.g., U.S. Pat. Nos. 7,663,010 and 8,183,424, the relevant contents of which are incorporated herein by reference.

In various embodiment of the process of the first aspect of this disclosure, at least a portion of the first C8+ aromatic hydrocarbon stream can be obtained from a toluene disproportionation process. In such embodiments, step (I) may comprise the following: (I-i) feeding toluene into a first toluene disproportionation zone; (I-j) converting at least a portion of the toluene in step (I-i) in the presence of a disproportionation catalyst under disproportionation conditions to produce a first disproportionation effluent comprising C7, C8, and C9+ aromatic hydrocarbons; (I-k) obtaining from the first disproportionation effluent a first disproportionation C8 stream consisting essentially of C8+ aromatic hydrocarbons; (I-l) obtaining at least a portion of the first C8+ hydrocarbon stream from the first disproportionation stream. Exemplary disproportionation zone, disproportionation catalysts, and disproportionation conditions can be found in, e.g., U.S. Pat. Nos. 6,486,373; 7,326,818; and 10,661,258, the relevant contents of which are incorporated herein by reference. The disproportionation catalyst can be shape-selective or non-shape-selective. If a shape-selective catalyst is used, the first disproportionation effluent may comprise p-xylene at a concentration significantly higher than m-xylene and/or o-xylene, and ethylbenzene at a low concentration, based on the total weight of all C8 aromatic hydrocarbons in the first disproportionation effluent, which can be highly advantageous for the purpose of co-production of a p-xylene product from the process of the first aspect of this disclosure.

In various embodiments of the process of the first aspect of this disclosure, at least a portion of the first C8+ hydrocarbon stream can be obtained from a benzene/toluene methylation process. In such embodiments, step (I) may comprise the following: (I-m) feeding C6-C7 aromatic hydrocarbons and a methylating agent (e.g., methanol, dimethylether, and mixtures thereof) into a first methylation zone; (I-n) reacting the C6-C7 aromatic hydrocarbons with the methylating agent in the first methylation zone in the presence of a first methylation catalyst under first methylation conditions to produce a first methylation effluent comprising C7 and C8 aromatic hydrocarbons; (I-o) obtaining from the first methylation effluent a first methylation C8+ stream consisting essentially of C8+ aromatic hydrocarbons; and (I-p) obtaining at least a portion of the first C8+ hydrocarbon stream from the first methylation C8+ stream. The methylation zone can include a fluid bed reactor, a moving bed reactor, a fixed bed reactor, and combinations thereof, and the like. Exemplary methylating agent, methylation zone, methylation catalysts, and methylation conditions can be found in, e.g., U.S. Pat. Nos. 5,939,597; 6,423,879; 6,504,072; 6,642,426; 7,799,962; 8,344,197; 9,095,831; 7,655,823; 7,176,339; 7,396,967; 7,902,414; 7,074,739; 7,276,638; 7,453,018; and 8,940,950, the relevant contents of which are incorporated herein by reference.

The methylation process can be particularly advantageously in providing at least a portion of the first C8+ hydrocarbon stream of step (I) of the processes of the first aspect of this disclosure, because the methylation catalyst and methylation conditions can be selected such that o-xylene is less favored compared to p-xylene that ethylbenzene can be produced a very low quantity. Thus, the methylation effluent can advantageously comprise o-xylene at a concentration significantly lower than that of p-xylene, and ethylbenzene at a negligible concentration. Thus, in certain embodiments, wherein in step (X), the second methylation C8+ stream can have at least one of the following features:

(a) an o-xylene concentration from $c(oX)1$ wt % to $c(oX)2$ wt %, based on the total weight of the second methylation C8+ stream, wherein $c(oX)1$ and $c(oX)2$ can be, independently, e.g., 0, 0.02, 0.04, 0.01, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, as long as $c(oX)1<c(oX)2$;

(b) an m-xylene concentration from $c(mX)1$ wt % to $c(mX)2$ wt %, based on the total weight of the second methylation C8+ stream, wherein $c(mX)1$ and $c(mX)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 25, 30, 35, 40, 45, 50, 55, as long as $c(mX)1<c(mX)2$;

(c) a p-xylene concentration from $c(pX)1$ wt % to $c(pX)2$ wt %, based on the total weight of the second methylation C8+ stream, wherein $c(pX)1$ and $c(pX)2$ can be, independently, e.g., 20, 25, 30, 35, 40, 45, 50, 55, 60, 65, 70, 75, 80, 85, 90, 95, 97, 98, 99, as long as $c(pX)1<c(pX)2$;

(d) an m-xylene/o-xylene ratio from $r(m/o)1$ to $r(m/o)2$, where $r(m/o)1$ and $r(m/o)2$ can be, independently, e.g., 2.1, 2.5, 3.0, 3.5, 4.0, 4.5, 5.0, 6.0, 7.0, 7.5, 8.0, 9.0, 10, 11, 12, 12.5, 13, 14, 15, 16, 17, 17.5, 18, 19, 20, as long as $r(m/o)1<r(m/o)2$;

(e) an ethylbenzene concentration from $c(EB)1$ wt % to $c(EB)2$ wt %, based on the total weight of the second methylation C8+ stream, wherein $c(EB)2$ and $c(EB)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, as long as $c(EB)1<c(EB)2$; and (f) a non-aromatic hydrocarbons concentration from $c(nA)1$ wt % to $c(nA)2$ wt %, based on the total weight of the second methylation C8+ stream, wherein $c(nA)1$ and $c(nA)8$ can be, independently, e.g., 0, 0.02, 0.04, 0.05, 0.06, 0.08, 0.1, 0.2, 0.4, 0.5, 0.6, 0.8, 1, 2, 3, 4, 5, as long as $c(nA)1<c(nA)2$.

In various other embodiments of the processes of the first aspect of this disclosure, it is desirable that the first C8+ hydrocarbon stream comprises non-aromatic hydrocarbons, especially linear paraffins, at a relatively low concentration. To that end, step (I) can comprise: (I-q) providing a precursor C8+ hydrocarbon stream comprising non-aromatic hydrocarbons; and (I-r) removing at least a portion of the non-aromatic hydrocarbons from the precursor C8+ hydrocarbon stream to obtain at least a portion of the first C8+ hydrocarbon stream. Step (I-r) can be carried out by using separation technologies such as solvent extraction separation, membrane separation, and adsorption chromatographic separation, any combinations thereof, and the like. Solvent extraction separation can be liquid-liquid extraction whereby a liquid solvent stream contacts a liquid stream of the precursor C8+ hydrocarbon stream in a counter-current fashion, extraction distillation assisted by a solvent, combinations thereof, and the like. Description of exemplary liquid-liquid separation process for separating non-aromatic hydrocarbons from a mixture of non-aromatic hydrocarbons and aromatic hydrocarbons can be found in, e.g., Handbook of Petrochemicals Production Processes, Second Edition, by Robert A. Meyers, Ph.D., Chapter 1.5, the relevant contents of which are incorporated herein by reference. Description of exemplary extraction distillation separation process for separating non-aromatic hydrocarbons from a mixture of non-aromatic hydrocarbons and aromatic hydrocarbons can be found in, e.g., Handbook of Petrochemicals Production Processes, Second Edition, by Robert A. Meyers, Ph.D., Chapter 1.13, the relevant contents of which are incorporated herein by reference. Description of exemplary membrane separation process for separating non-aromatic hydrocarbons from a mixture of non-aromatic hydrocarbons and aromatic hydrocarbons can be found in, e.g., U.S. Pat. Nos. 4,571,444; 6,187,987; and 6,180,008; and Zhang, Fan, "Selective Separation of Toluene/n-Heptane by Supported Ionic Liquid Membranes with [Bmim][BF4]," Chem. Eng. Technol. 2015, 38, No. 2, 355-361, the relevant contents of which are incorporated herein by reference. Description of exemplary adsorption chromatographic separation process for separating non-aromatic hydrocarbons from a mixture of non-aromatic hydrocarbons and aromatic hydrocarbons can be found in, e.g., Handbook of Petrochemicals Production Processes, Second Edition, by Robert A. Meyers, Ph.D., Chapter 1.13, the relevant content of which are incorporated herein by reference.

Step (II)

Step (II) of the processes of the first aspect of this disclosure can comprise feeding the first C8+ hydrocarbon stream into a C8 splitter to obtain a first o-xylene-rich stream depleted in p-xylene and m-xylene, and a first o-xylene-depleted stream rich in p-xylene and m-xylene. The C8 splitter can include one or more distillation columns. The C8 splitter may additionally or alternatively comprise separation devices using membrane separation technology or adsorption chromatographic separation technology. The o-xylene-rich stream is rich in o-xylene and depleted in p-xylene and m-xylene compared to the first C8+ hydrocarbon stream, and the o-xylene-depleted stream is depleted in o-xylene and rich in p-xylene and m-xylene compared to the first C8+ hydrocarbon stream.

O-xylene, m-xylene, p-xylene, and ethylbenzene have normal boiling points of 144° C., 139° C., 138° C., and 136° C., respectively. Separation of o-xylene from a mixture of p-xylene, m-xylene, and ethylbenzene can be achieved using a distillation column. It is desirable that the ratio of the o-xylene quantity in the o-xylene-rich stream to the o-xylene quantity in the o-xylene-depleted stream can range from r1 to r2, where r1 and r2 can be, independently, e.g., 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, as long as r1≥r2. Preferably r1≥1. More preferably r1≥2. More preferably r1≥5. Still more preferably r1≥10. It is desirable that the ratio of the o-xylene concentration in the o-xylene-rich stream, based on the total weight of the o-xylene-rich stream, to the o-xylene concentration in the o-xylene-depleted stream can range from R1 to R2, where R1 and R2 can be, independently, e.g., 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, as long as R1<R2. A low quantity, preferably a low concentration of o-xylene in the o-xylene-depleted stream compared to in the o-xylene-rich stream is conducive for the production of a high-octane aviation gasoline blend stock using the processes of this disclosure.

From the C8 splitter, additional streams other than the o-xylene-rich stream depleted p-xylene and m-xylene and the o-xylene-depleted stream rich in p-xylene and m-xylene may be produced. For example, it is contemplated that from the C8 splitter, an additional stream rich in C9+ hydrocarbons but depleted in C8 hydrocarbons compared to the first C8+ hydrocarbon stream, may be produced.

In various other embodiments of the first aspect of this disclosure, in step (II), the first o-xylene-depleted stream can comprise o-xylene at a concentration from $c(oX)1$ wt % to $c(oX)2$ wt %, based on the total weight of the first o-xylene-depleted stream, where $c(oX)1$ and $c(oX)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, as long as $c(oX)1<c(oX)2$.

In various other embodiments of the first aspect of this disclosure, in step (II), the first o-xylene-depleted stream can comprise p-xylene at a concentration from $c(pX)1$ wt % to $c(pX)2$ wt %, m-xylene at a concentration from $c(mX)1$ wt % to $c(mX)2$ wt %, based on the total weight of the first o-xylene-depleted stream, where $c(pX)1$ and $c(pX)2$ can be, independently, e.g., 24, 25, 26, 28, 30, 32, 34, 35, 36, 38, 40, 45, 50, 55, 60, 65, 70, 75, 80, 85, 90, 95, 99, as long as $c(pX)1<c(pX)2$; and $c(mX)1$ and $c(mX)2$ can be, independently, e.g., 50, 52, 54, 55, 56, 58, 60, 62, 64, 65, 66, 68, 70, 75, 80, 85, 90, 95, 96, 97, 98, 99, as long as $c(mX)1<c(mX)2$.

In various other embodiments of the first aspect of this disclosure, in step (II), the first o-xylene-depleted stream can comprise ethylbenzene at a concentration from $c(EB)1$ wt % to $c(EB)2$ wt %, based on the total weight of the first o-xylene-depleted stream, where $c(EB)1$ and $c(EB)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 11, 12, 13, 14, 15, 16, 17, 18, 19, 20, 21, 22, 23, 24, 25, as long as $c(EB)1<c(EB)2$.

In various other embodiments of the first aspect of this disclosure, in step (II), the first o-xylene-depleted stream can comprise non-aromatic hydrocarbons at a concentration from $c(nA)1$ wt % to $c(nA)2$ wt %, based on the total weight of the first o-xylene-depleted stream, where $c(nA)1$ and $c(nA)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 15, 20, 25, as long as $c(nA)1<c(nA)2$. In preferred embodiments, first o-xylene-depleted stream is essentially free of linear paraffins.

Step (III)

In preferred embodiments of the processes of this disclosure, step (III) is performed, in which the first o-xylene-depleted stream is supplied to a p-xylene recovery subsystem, from which a p-xylene product stream rich in p-xylene and a raffinate stream depleted in p-xylene are obtained. Such embodiments including step (III) have the advantage of producing, in addition to high-octane-number fuel component(s), p-xylene product(s). Indeed, one can adjust the quantities of the various streams conducted away for producing high octane-number fuel component(s), e.g., the first o-xylene-depleted stream of step (II), the raffinate stream of step (III), and the like, for the purpose of adjusting the relative quantities of the p-xylene product(s) and the high-octane-number fuel component product(s).

Various technologies are available to recover a high-purity p-xylene product from a C8 aromatic hydrocarbon mixture, e.g., a xylenes mixture such as a xylenes mixture rich in p-xylene and m-xylene but depleted in o-xylene. A category of such technologies, based on crystallization, takes advantage of the much higher melting point of p-xylene (13° C.) than those of o-xylene (−25° C.), m-xylene (−48° C.), and ethylbenzene (−95° C.), by cooling a C8 aromatic hydrocarbon mixture to a temperature lower than p-xylene crystallization temperature to preferentially crystallize p-xylene out of the mixture, followed by separation of the p-xylene crystals from the residual liquid by filtration, centrifugation, and the like. The p-xylene crystals, upon optional additional purification (e.g., by melting and recrystallization), can be used as a high purity p-xylene product. The residual liquid, containing p-xylene at various concentrations, is called a filtrate or a raffinate herein interchangeably. Description of crystallization-based p-xylene recovery sub-system and processes can be found in, e.g., Handbook of Petrochemicals Production Processes, Second Edition, by Robert A. Meyers, Ph.D., Chapter 1.5, the relevant contents of which are incorporated herein by reference. In embodiments where the p-xylene recovery subsystem can comprise a crystallization separation stage, the raffinate stream can comprise p-xylene at a concentration from $c(pX)5$ wt % to $c(pX)6$ wt %, and m-xylene at a concentration from $c(m)5$ wt % to $c(m)6$ wt %, based on the total weight of the raffinate stream, where $c(pX)5$ and $c(pX)6$ can be, independently, e.g., 8, 9, 10, 11, 12, 13, 14, 15, 16, 18, 20, 22, 24, 25, 26, 28, 30, 32, 34, as long as $c(pX)5 < c(pX)6$; and $c(mX)5$ and $c(m)6$ can be, independently, e.g., 60, 65, 70, 75, 80, 85, 90, 91, 92, as long as $c(mX)5 < c(mX)6$. Such a raffinate stream, due to its relatively low concentrations of p-xylene and o-xylene, is particularly advantageous for use as a high-octane-number fuel component, particularly a high-octane-number AvGas component.

Another category of p-xylene recovery technology is based on adsorption chromatography, which takes advantage of the differential affinity of p-xylene to an adsorption matrix material relative to its isomers. Likewise, a high-purity p-xylene product stream and a residual stream, called raffinate herein, are produced. Description of adsorption chromatographic p-xylene recovery sub-system and processes can be found in, e.g., U.S. Pat. Nos. 5,849,981; 4,886,929; and 3,686,342; WO201547680; WO201313492; WO201313493; and WO200836913, the relevant contents of which are incorporated herein by reference. In embodiments where the p-xylene recovery subsystem can comprise an adsorption chromatographic separation stage, the raffinate stream can comprise p-xylene at a concentration from $c(pX)3$ wt % to $c(pX)4$ wt %, and m-xylene at a concentration from $c(mX)3$ wt % to $c(mX)4$ wt %, based on the total weight of the raffinate stream, where $c(pX)3$ and $c(pX)4$ can be, independently, e.g., 0, 0.1, 0.2, 0.4, 0.5, 0.6, 0.8, 1, 2, 3, 4, 5, as long as $c(pX)3 < c(pX)4$; and $c(mX)3$ and $c(mX)4$ can be, independently, e.g., 60, 65, 70, 75, 80, 85, 90, 91, 92, 93, 94, 95, as long as $c(mX)3 < c(mX)4$. Such a raffinate stream, due to its low concentrations of p-xylene and o-xylene, is particularly advantageous for use as a high-octane-number fuel component, particularly a high-octane-number AvGas component, alone or in combination with other streams, such as the first o-xylene-depleted stream.

Step (IV)

In step (IV), the high-octane-number fuel component can be obtained from one or more of: the first o-xylene-depleted stream; the raffinate stream; and a mixture of the first o-xylene-depleted stream and the raffinate stream at any proportion. Thus, at least a portion of the first o-xylene-depleted stream, or at least a portion of the raffinate stream described above may be conducted away and used as is as a high-octane-number fuel component. Alternatively, at least portion of the first o-xylene-depleted stream and a portion of the raffinate stream may be mixed at any suitable proportion to produce a high-octane-number fuel component, particularly a high-octane number AvGas component.

In certain embodiments, step (IV) can include (IV-a) abating at least a portion of the ethylbenzene, if any, from at least a portion of one or more of: the first o-xylene-depleted stream; the raffinate stream; and a mixture of the first o-xylene-depleted stream and the raffinate stream at any proportion, to obtain an ethylbenzene-abated C8 stream; and (IV-b) providing at least a portion of the ethylbenzene-abated C8 stream as at least a portion of the high-octane-number fuel component. In various embodiments, step (IV-a) can comprise one or more of: (IV-a-1) converting at least a portion of the ethylbenzene into benzene; (IV-a-2) converting at least a portion of the ethylbenzene into toluene; (IV-a-3) separating at least a portion of the ethylbenzene using a membrane and/or by distillation; and (IV-a-4) separating at least a portion of the ethylbenzene using an adsorption chromatography separator.

Description of processes, catalysts, and reaction conditions for converting ethylbenzene into benzene useful for step (IV-a-1) can be found in, e.g., U.S. Pat. No. 8,835,705, the relevant contents of which are incorporated herein by reference.

Description of processes, catalysts, and reaction conditions for converting ethylbenzene into toluene useful for step (IV-a-2) can be found in, e.g., U.S. Provisional Patent Application No. 62/876,391, having a filing date of Jul. 19, 2019 and entitled "Processes for Converting Aromatic Hydrocarbons via Alkyl-Demethylation,", the relevant contents of which are incorporated herein by reference.

Description of exemplary processes and membranes for separating ethylbenzene useful for step (IV-a-3) can be found in, e.g., U.S. Patent Application Publication No. US2017/0247303A1, the relevant contents of which are incorporated herein by reference.

Description of exemplary processes, adsorbents, and equipment for separating ethylbenzene useful for step (IV-a-4) can be found in, e.g., U.S. Pat. No. 4,613,725, the relevant contents of which are incorporated herein by reference.

Steps (V) to (VII)

In various preferred embodiments of the processes of the first aspect of this disclosure, steps (V) to (VII) described summarily above are performed. The isomerization conditions can include a temperature and a pressure such that a majority of the C8 aromatic hydrocarbons in the isomerization zone are in vapor phase ("vapor-phase isomerization" or "VPI"). Alternatively, the isomerization conditions can include a temperature and a pressure such that a majority of the C8 aromatic hydrocarbons in the isomerization zone are in liquid phase ("liquid-phase isomerization" or "LPI"). LPI requires a lower temperature than VPI, and can be carried out without co-feeding a molecular hydrogen stream into the isomerization zone. As such LPI may be preferred in certain embodiments over VPI, especially where the raffinate stream comprises ethylbenzene at a low concentration. The VPI may be favored where the raffinate comprises ethylbenzene at a high concentration, e.g., 10 wt %, based on the total weight of the raffinate stream, because VPI can be more effective than LPI in converting ethylbenzene. Description of exemplary VPI processes and catalysts can be found in, e.g., U.S. Patent Application Publication Nos. US20110319688A1; US20120108867A1; US20120108868A1; US20140023563A1; US20150051430A1; and US20170081259A1; the relevant contents of which are incorporated herein by reference. Description of exemplary LPI processes and catalysts can be found in, e.g., U.S. Patent Application Publication Nos. US20110319688A1; US20120108867A1; US20130274532A1; US20140023563A1; and US20150051430A1, the relevant contents of which are incorporated herein by reference.

In the isomerization zone, a portion of the m-xylene contained in the raffinate is converted into p-xylene and optionally o-xylene. In various embodiments, the second C8+ hydrocarbon stream can comprise o-xylene at a concentration from $c(oX)3$ wt % to $c(oX)4$ wt %, based on the total weight of the second C8+ hydrocarbon stream, where $c(oX)3$ and $c(oX)4$ can be, independently, e.g., 2, 3, 4, 5, 6, 7, 8, 9, 10, 12, 14, 15, 16, 18, 20, 22, 24, 25, 26, as long as $c(oX)3<c(oX)4$. In various embodiments, the second C8+ hydrocarbon stream can comprise p-xylene at a concentration from $c(pX)7$ wt % to $c(pX)8$ wt %, m-xylene at a concentration from $c(mX)7$ wt % to $c(mX)8$ wt %, based on the total weight of the second C8+ hydrocarbon stream, where $c(pX)7$ and $c(pX)8$ can be, independently, e.g., 5, 6, 7, 8, 9, 10, 12, 14, 15, 16, 18, 20, 22, 24, as long as $c(pX)7<c(pX)8$; and $c(mX)7$ and $c(mX)8$ can be, independently, e.g., 50, 55, 60, 65, 70, 75, 80, 85, 90, 91, 92, 93, as long as $c(mX)7<c(mX)8$. In various embodiments, the second C8+ hydrocarbon stream can comprise ethylbenzene at a concentration from $c(EB)3$ wt % to $c(EB)4$ wt %, based on the total weight of the second C8+ hydrocarbon stream, where $c(EB)3$ and $c(EB)4$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 21, as long as $c(EB)3<c(EB)4$. In various embodiments, the second C8+ hydrocarbon stream can comprise non-aromatic hydrocarbons at a concentration from $c(nA)3$ wt % to $c(nA)4$ wt %, based on the total weight of the second C8+ hydrocarbon stream, where $c(nA)3$ and $c(nA)4$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, as long as $c(nA)3<c(nA)4$. In various embodiments, the second C8+ hydrocarbon stream is essentially free of linear paraffins. In various embodiments, the second C8+ hydrocarbon stream thereby may preferably comprise o-xylene, m-xylene, and p-xylene at approximately equilibrium concentrations thereof (i.e., about 24% p-xylene, about 26% o-xylene, and about 50% of m-xylene, based on the total weight of all xylenes).

Steps (VIII)-(XI)

In various preferred embodiments of the processes of the first aspect of this disclosure, steps (V) to (VII) described summarily above are performed. In these embodiments, a C8+ hydrocarbon stream comprising ≥25 wt % of p-xylene, based on all xylenes therein, is produced from a shape-selective toluene disproportionation process in the presence of a shape-selective disproportionation catalyst in a disproportionation zone, which is advantageously directly fed into the p-xylene recovery sub-system, from which a p-xylene product is produced. The C8+ hydrocarbon stream producible from a shape-selective toluene disproportionation process can be advantageously low in ethylbenzene and o-xylene as well, making it especially suitable as a component for high-octane-number fuel blend. A raffinate stream from the p-xylene recovery sub-system upon recovery of a majority of the p-xylene from the C8+ hydrocarbon stream produced from shape-selective toluene disproportionation process can be advantageously low in p-xylene, o-xylene, and ethylbenzene, rendering it particularly suitable as a high-octane number fuel component, particularly a high-octane-number AvGas component. Description of exemplary shape-selective disproportionation catalysts and disproportionation conditions can be found in, e.g., U.S. Pat. Nos. 7,326,818 and 10,661,258, the relevant contents of which are incorporated herein by reference.

In various embodiments, in step (X), the second disproportionation C8+ stream can comprise o-xylene at a concentration from $c(oX)5$ wt % to $c(oX)6$ wt %, based on the total weight of the second disproportionation C8+ stream, wherein $c(oX)5$ and $c(oX)6$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, 26, as long as $c(oX)5<c(oX)6$. In various embodiments, in step (X), the second disproportionation C8+ stream can comprise p-xylene at a concentration from $c(pX)9$ wt % to $c(pX)10$ wt %, based on the total weight of the second disproportionation C8+ stream, wherein $c(pX)9$ and $c(pX)10$ can be, independently, e.g., 25, 26, 28, 30, 35, 40, 45, 50, 55, 60, 65, 70, 75, 80, 85, 90, 95, 96, 97, as long as $c(pX)9<c(pX)10$. In various embodiments, in step (X), the second disproportionation C8+ stream can comprise ethylbenzene at a concentration from $c(EB)9$ wt % to $c(EB)10$ wt %, based on the total weight of the second disproportionation C8+ stream, wherein $c(EB)9$ and $c(EB)10$ can be, independently, e.g., 0, 0.02, 0.04, 0.05, 0.06, 0.08, 0.1, 0.2, 0.4, 0.5, 0.6, 0.8, 1, 2, 3, 4, 5, as long as $c(EB)9<c(EB)10$. In various embodiments, in step (X), the second disproportionation C8+ stream can comprise non-aromatic hydrocarbons at a total concentration from $c(nA)9$ wt % to $c(nA)10$ wt %, based on the total weight of the second disproportionation C8+ stream, wherein $c(nA)9$ and $c(nA)10$ can be, independently, e.g., 0, 0.02, 0.04, 0.05, 0.06, 0.08, 0.1, 0.2, 0.4, 0.5, 0.6, 0.8, 1, 2, 3, 4, 5, as long as $c(nA)9<c(nA)10$. In various embodiments, in step (X), the second disproportionation C8+ stream can exhibit a m-xylene/o-xylene molar ratio in a range from r1 to r2, wherein r1 and r2 can be, independently, 2, 3, 4, 5, 6, 7, 8, 9, 10, 11, 12, 13, 14, 15, 16, 17, 18, 19, 20, as long as $r1<r2$; preferably $r1 \geq 5$, more preferably $r1 \geq 8$.

Steps (XII)-(XV)

In various embodiments of the process of the first aspect of this disclosure, steps (XII)-(XV) are performed, which includes a step of methylating C6-C7 aromatic hydrocarbon(s) to produce C8+ aromatic hydrocarbons by contacting a methylating agent in the presence of a methylation catalyst under methylation conditions. The methylation catalyst and conditions can be chosen such that the methylation effluent can comprise p-xylene at a high concentration, and o-xylene and ethylbenzene at relatively low concentrations. The second methylation C8+ stream therefore can be advantageously directly used as a high-octane-number fuel component. A raffinate stream from the p-xylene recovery sub-system upon recovery of a majority of the p-xylene from the second methylation C8+ stream can be advantageously low in p-xylene, o-xylene, and ethylbenzene, rendering it particularly suitable as a high-octane-number fuel component. Description of exemplary methylation catalysts, methylating agent, and methylation conditions can be found in, e.g., U.S. Pat. Nos. 6,423,879; 6,504,072; 6,642,426, and 9,440,893, the relevant contents of which are incorporated herein by reference.

In various embodiments, in step (XII), the second methylation C8+ stream can have at least one of the following features:

(a) an o-xylene concentration from $c(oX)1$ wt % to $c(oX)2$ wt %, based on the total weight of the second methylation C8+ stream, wherein $c(oX)1$ and $c(oX)2$ can be, independently, e.g., 0, 0.02, 0.04, 0.01, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, 26, as long as $c(oX)1 < c(oX)2$;

(b) an m-xylene concentration from $c(mX)1$ wt % to $c(mX)2$ wt %, based on the total weight of the second methylation C8+ stream, wherein $c(mX)1$ and $c(mX)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, 26, as long as $c(mX)1 < c(mX)2$;

(c) a p-xylene concentration from $c(pX)1$ wt % to $c(pX)2$ wt %, based on the total weight of the second methylation C8+ stream, wherein $c(pX)1$ and $c(pX)2$ can be, independently, e.g., 25, 30, 35, 40, 45, 50, 55, 60, 65, 70, 75, 80, 85, 90, 91, 92, 93, 94, 95, as long as $c(pX)1 < c(pX)2$;

(d) an m-xylene/o-xylene ratio from $r(m/o)1$ to $r(m/o)2$, where $r(m/o)1$ and $r(m/o)2$ can be, independently, e.g., 2.1, 2.5, 3.0, 3.5, 4.0, 4.5, 5.0, 6.0, 7.0, 7.5, 8.0, 9.0, 10, 11, 12, 12.5, 13, 14, 15, 16, 17, 17.5, 18, 19, 20, as long as $r(m/o)1 < r(m/o)2$;

(e) an ethylbenzene concentration from $c(EB)1$ wt % to $c(EB)2$ wt %, based on the total weight of the second methylation C8+ stream, wherein $c(EB)2$ and $c(EB)2$ can be, independently, e.g., 0, 0.02, 0.04, 0.05, 0.06, 0.08, 0.1, 0.2, 0.4, 0.5, 0.6, 0.8, 1, 2, 3, 4, 5, as long as $c(EB)1 < c(EB)2$; and (f) a non-aromatic hydrocarbons concentration from $c(nA)1$ wt % to $c(nA)2$ wt %, based on the total weight of the second methylation C8+ stream, wherein $c(nA)1$ and $c(nA)8$ can be, independently, e.g., 0, 0.02, 0.04, 0.05, 0.06, 0.08, 0.1, 0.2, 0.4, 0.5, 0.6, 0.8, 1, 2, 3, 4, 5, as long as $c(nA)1 < c(nA)2$.

Steps (XVI)-(XVII)

In various embodiments of the process of the first aspect of this disclosure, the first C8+ hydrocarbon stream can comprise C9+ hydrocarbons, the first o-xylene-rich stream can comprise C9+ hydrocarbons, and the process further can comprise steps (XVII) and (XVIII) described summarily above. In preferred embodiments, the separating of the first o-xylene-rich stream to obtain the o-xylene product stream and the C9+ hydrocarbon stream can be conveniently carried out using a distillation column. Other separating means and processes, such as membrane separation, adsorption chromatographic separation, may be used alternatively or additionally as appropriate. In these embodiments, an o-xylene product can be produced, and a portion of the C9+ hydrocarbon stream can be used as at least a portion of the high-octane-number fuel component, alone or in combination with other suitable streams as described above. The C9+ hydrocarbon stream can comprise, e.g., trimethylbenzenes, at appreciable quantity, which, upon further optional separation, can be particularly useful as a high-octane-number fuel component, particularly a high-octane-number AvGas component. The C9+ hydrocarbon stream, or a portion thereof, may be fed into a transalkylation process as described above as well.

4.2 The Processes of the Second Aspect of This Disclosure

The second aspect of this disclosure relates to a process for producing a high-octane-number aviation gasoline component, the process comprising:

(A) feeding toluene into a toluene disproportionation zone;

(B) converting at least a portion of the toluene in the presence of a shape selective catalyst to produce a disproportionation effluent comprising C7, C8, and C9+ aromatic hydrocarbons;

(C) obtaining from the disproportionation effluent a disproportionation C8+ stream consisting essentially of C8+ aromatic hydrocarbons having a p-xylene concentration of at least 25 wt %, based on the total weight of the second disproportionation C8+ stream;

(D) feeding at least a portion of the disproportionation C8+ stream to a p-xylene recovery sub-system, from which a p-xylene product stream rich in p-xylene and a raffinate stream depleted in p-xylene are obtained; and (E) obtaining at least a portion of the high-octane-number fuel component from the raffinate stream.

In various embodiments of the processes of the second aspect of this disclosure, steps (A) to (C) can be the same or similar to steps (VIII) to (XI) in embodiments of the processes of the first aspect of this disclosure as described above.

In various embodiments of the process of the second aspect of this disclosure, other steps in embodiments of the processes of the first aspect of this disclosure may be performed as appropriate.

4.3 The Processes of the Third Aspect of This Disclosure

The third aspect of this disclosure relates to a process for producing a high-octane-number fuel component, particularly a high-octane-number AvGas component, the process comprising:

(a) feeding C6-C7 aromatic hydrocarbon(s) and a methylating agent into a methylation zone;

(b) reacting the C6-C7 aromatic hydrocarbons with the methylating agent in the methylation zone in the presence of a methylation catalyst under methylation conditions to produce a methylation effluent comprising C7 and C8+ aromatic hydrocarbons;

(c) obtaining from the methylation effluent a methylation C8+ stream consisting essentially of C8+ aromatic hydrocarbons having a p-xylene concentration of at least 25 wt % wt %, based on the total weight of the methylation C8+ stream;

(d) feeding at least a portion of the methylation C8+ stream to a p-xylene recovery sub-system, from which a p-xylene product stream rich in p-xylene and a raffinate stream depleted in p-xylene are obtained; and (e) obtaining at least a portion of the high-octane-number fuel component from the raffinate stream.

In various embodiments of the processes of the second aspect of this disclosure, steps (a) to (c) can be the same or similar to steps (XII) to (XIV) in various embodiments of the processes of the first aspect of this disclosure as described above.

In various embodiments of the process of the third aspect of this disclosure, other steps in embodiments of the processes of the first aspect of this disclosure may be performed as appropriate.

4.4 The Processes of the Fourth Aspect of This Disclosure

The fourth aspect of this disclosure relates to a process for producing a high-octane-number fuel component, particularly a high-octane-number AvGas component, the process comprising:

(1) providing a C8 aromatic hydrocarbon stream comprising p-xylene, o-xylene, m-xylene, and optionally ethylbenzene;

(2) feeding the C8 aromatic hydrocarbon stream to a p-xylene recovery sub-system, from which a p-xylene product stream rich in p-xylene and a raffinate stream depleted in p-xylene are obtained; and (3) obtaining the high-octane-number fuel component from one or more of: at least a portion of the C8 aromatic hydrocarbon stream; at least a portion of the raffinate stream; and a mixture of at least a portion of the C8 aromatic hydrocarbon stream and at least a portion of the raffinate stream.

In various embodiments of the processes of the fourth aspect, the following steps may be included:

(4) feeding at least a portion of the raffinate stream to an isomerization zone operated under isomerization conditions to convert at least a portion of m-xylene in the raffinate stream into p-xylene and/or at least a portion of ethylbenzene, if any, in the raffinate stream into at least one of benzene, toluene, and/or xylenes, to obtain an isomerization effluent stream comprising mixed xylenes; and (5) obtaining at least a portion of the C8 aromatic hydrocarbon stream from the isomerization effluent stream.

In various embodiments of the processes of the fourth aspect of this disclosure, steps (4) and (5) can substantially correspond to steps (V), (VI) and (VII) in embodiments of the processes of the first aspect of this disclosure as described above.

In various embodiments of the processes of the fourth aspect of this disclosure, step (1) can comprise:

(1a) providing a first C8+ hydrocarbon stream comprising p-xylene, o-xylene, m-xylene, and optionally ethylbenzene;

(1b) feeding the first C8+ hydrocarbon stream into a C8 splitter to obtain a first o-xylene-rich stream depleted in p-xylene and m-xylene, and a first o-xylene-depleted stream rich in p-xylene and m-xylene; and (1c) providing at least a portion of the first o-xylene-depleted stream as at least a portion of the C8 aromatic hydrocarbon stream.

In various embodiments of the processes of the fourth aspect of this disclosure, steps (1a) and (1b)) can substantially correspond to steps (I) and (II) in embodiments of the processes of the first aspect of this disclosure as described above.

In various embodiments of the process of the fourth aspect of this disclosure, other steps in embodiments of the processes of embodiments of the first aspect of this disclosure may be performed as appropriate.

In various embodiments of the processes of the fourth aspect of this disclosure, the C8 aromatic hydrocarbon stream comprises o-xylene at a concentration from $c(oX)1$ wt % to $c(oX)2$ wt %, based on the total weight of the first o-xylene-depleted stream, where $c(oX)1$ and $c(oX)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, as long as $c(oX)1<c(oX)2$.

In various embodiments of the processes of the fourth aspect of this disclosure, the C8 aromatic hydrocarbon stream comprises p-xylene at a concentration from $c(pX)1$ wt % to $c(pX)2$ wt %, m-xylene at a concentration from $c(mX)1$ wt % to $c(mX)2$ wt %, based on the total weight of the first o-xylene-depleted stream, where $c(pX)1$ and $c(pX)2$ can be, independently, e.g., 24, 25, 26, 28, 30, 32, 34, 35, 36, 38, 40, 45, 50, 55, 60, 65, 70, 75, 80, 85, 90, 95, 99, as long as $c(pX)1<c(pX)2$; and $c(mX)1$ and $c(mX)2$ can be, independently, e.g., 50, 52, 54, 55, 56, 58, 60, 62, 64, 65, 66, 68, 70, 75, 80, 85, 90, 95, 96, 97, 98, 99, as long as $c(mX)1<c(mX)2$.

In various embodiments of the processes of the fourth aspect of this disclosure, the C8 aromatic hydrocarbon stream comprises ethylbenzene at a concentration from $c(EB)1$ wt % to $c(EB)2$ wt %, based on the total weight of the first o-xylene-depleted stream, where $c(EB)1$ and $c(EB)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 11, 12, 13, 14, 15, 16, 17, 18, 19, 20, 21, 22, 23, 24, 25, as long as $c(EB)1<c(EB)2$.

In various embodiments of the processes of the fourth aspect of this disclosure, the C8 aromatic hydrocarbon stream comprises non-aromatic hydrocarbons at a concentration from $c(nA)1$ wt % to $c(nA)2$ wt %, based on the total weight of the first o-xylene-depleted stream, where $c(nA)1$ and $c(nA)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 15, 20, 25, as long as $c(nA)1<c(nA)2$.

In various embodiments of the processes of the fourth aspect of this disclosure, the C8 aromatic hydrocarbon stream is essentially free of linear paraffins.

5. Detailed Description of the Processes/Systems Illustrated in the FIGURE

Referring to the FIGURE, in an exemplary process 101 of this disclosure for making a high-octane-number fuel component, C8+ hydrocarbon streams 103, 105, and 107, comprising p-xylene, o-xylene, and m-xylene, and optionally ethylbenzene, at various concentrations thereof, are supplied separately (as shown) or jointly in any combination (not shown) into a C8 splitter 109. Streams 103, 105, and 107 may be sourced from the same, similar, or different process/units, e.g., a transalkylation process/unit, a non-selective toluene process/disproportionation unit, a selective toluene disproportionation process/unit, a C8 aromatics isomerization process/unit, a toluene/benzene alkylation process/unit (such as a toluene alkylation with methanol process/unit), a reforming process/unit, and any combinations thereof. The C8 splitter 109 can comprise, e.g., a distillation column, a membrane separator, an adsorption chromatographic separation unit, or any combinations thereof. Preferably the C8 splitter 109 comprises a distillation column. From the C8 splitter 109, an o-xylene-rich stream 113 depleted in p-xylene and m-xylene (e.g., a bottoms stream if the C8 splitter 109 is a distillation column) and an o-xylene-depleted stream 111 rich in p-xylene and m-xylene (e.g., an overheads stream if the C8 splitter 109 is a distillation column) are produced. Additional stream(s) (now shown) may be produced from the C8 splitter 109 as well.

Stream 111 may comprise ethylbenzene at various concentrations. Where stream 111 comprises ethylbenzene at a significant concentration, e.g., ≥5 wt %, or ≥10 wt %, based on the total weight of stream 111, it may be desirable to abate the ethylbenzene in unit 121 to produce a C8 stream 123 having ethylbenzene at a reduced concentration compared to stream 111. Unit 121 can abate ethylbenzene by one or more means known in the industry, including but not limited to solvent assisted extraction, adsorption chromatographic separation, and chemical conversion into benzene, toluene, xylenes, and the like in the presence of certain catalysts. Streams 111 and/or stream 123 desirably have relatively low o-xylene and ethylbenzene concentrations, and therefore can be advantageously used as a high-octane-number fuel component or a portion thereof. As shown in the FIGURE, a split stream 125 from stream 123, can be conducted away for that purpose. Alternatively or additionally (now shown), unit 121 or a similar unit can be used to receive stream 125, abate a portion of the ethylbenzene therein, to obtain a stream with reduced concentration of ethylbenzene suitable as a high-octane-number fuel component.

As shown in the FIGURE, a toluene stream 147 is supplied into a selective toluene disproportionation unit 149, where toluene undergoes disproportionation reaction in the presence of a shape-selective disproportionation catalyst under suitable disproportionation conditions to produce a disproportionation effluent 151 comprising toluene, p-xylene, m-xylene, o-xylene, and optionally C9+ aromatic hydrocarbons. As a result of the use of a shape selective disproportionation catalyst, preferably among all xylenes in stream 151, p-xylene has a weight percentage ≥25 wt %, ≥30 wt %, ≥40 wt %, ≥50 wt %, ≥60 wt %, ≥75 wt %, ≥80 wt %, ≥90 wt %, or even ≥95 wt %. Stream 151 is then separated in a separator (e.g., a distillation column) 153 to obtain a C8 hydrocarbon stream 155 consisting essentially of xylenes. Stream 155 may be suitable as a high-octane-number fuel component per se. Thus, as shown in the FIGURE, a split stream 157 from stream 155 may be conducted away as a high-octane-number fuel component.

As shown in the FIGURE, streams 127 (a split stream of stream 123) and 159 (a split stream of stream 155), both comprising p-xylene at high concentrations and o-xylene at low concentrations, can be then supplied into a p-xylene recovery sub-system 121 as a joint stream 129 (as shown) or separately (not shown), from which a high-purity p-xylene product stream 133 and a raffinate stream 135 depleted in p-xylene and rich in m-xylene are produced. The p-xylene recovery sub-system can include, e.g., a crystallization separator, an adsorption chromatographic separator, or a combination of both, as known in the art. Stream 135, preferably having a low p-xylene concentration, a low o-xylene concentration, and a low ethylbenzene concentration, can be advantageously used as a high-octane-number fuel component per se. Where stream 135 comprises ethylbenzene at a relatively high concentration (e.g., ≥5 wt %, ≥8 wt %, ≥10 wt %), an ethylbenzene abating unit, unit 137, which can be similar to unit 121 described above, can be used to abate the ethylbenzene therein to obtain a stream 139 having a lower ethylbenzene concentration. A split stream 141 of stream 139 can be conducted away as a high-octane-number fuel component, or a portion thereof. Additionally or alternatively (now shown), unit 137 or a similar unit can be used to receive stream 141, abate a portion of the ethylbenzene therein, to obtain a stream with reduced concentration of ethylbenzene suitable as a high-octane-number fuel component. Alternatively or additionally, a mixture of a portion of stream 125 and a portion of stream 141 may be used as a high octane-number fuel component.

Stream 139 or a portion thereof (stream 143, as shown) may be supplied into a C8 aromatic hydrocarbons isomerization zone 145, where m-xylene contacts an isomerization catalyst under isomerization conditions and is partly converted into p-xylene to produce an isomerization effluent 129 comprising p-xylene, m-xylene, and o-xylene. The isomerization conditions can include temperature and pressure such that the C8 hydrocarbons are present substantially in liquid phase or vapor phase. Alternatively, a combination of an isomerization zone under liquid phase isomerization conditions and an isomerization zone under vapor phase isomerization conditions may be used. A C8 hydrocarbon stream 147 can be obtained from the effluent from the isomerization zone 145. Advantageously, stream 147 can comprise o-xylene, m-xylene, and p-xylene at concentrations close to their thermal equilibrium concentrations. Stream 147 is then advantageously supplied to C8 splitter 109.

The first o-xylene-rich stream 113 from the C8 splitter 109 can comprise, in addition to o-xylene, C9+ hydrocarbons at various concentrations. Thus, stream 109 can be supplied into an o-xylene recovery sub-system 115, from which a high-purity o-xylene product stream 117 and a C9+ hydrocarbon stream 119 can be obtained. The o-xylene recovery sub-system 115 can include, e.g., one or more of a distillation column, an adsorption chromatographic separator, a membrane separator, and combinations thereof. High-purity o-xylene Stream 117 can be used as is or subject to further purification for various applications, e.g., the production of phthalic acid, phallic anhydride, and the like. Stream 119, optionally upon further purification, separation, or processing, can be used as a high-octane-number fuel component, or supplied together with C6-C7 aromatic hydrocarbons into a transalkylation unit (not shown), from which additional xylenes can be produced. In a specific example, stream 119, optionally upon further separation and processing, can comprise substantial quantity of trimethylbenzenes, a hydrocarbon having very high octane number and valuable as a high-octane fuel component. Thus, alternatively and additionally, stream 119, or a portion thereof, optionally upon further purification and treatment, can be mixed with one or more of streams 125 and 141 (optionally upon further ethylbenzene abatement as described above) to form a high-octane-number fuel component.

The overall process/system of the FIGURE can be advantageously used to produce one or more of the following products: high-purity p-xylene; high-purity o-xylene; and high-octane-number fuel components. The high-octane-number fuel components made by the processes of this disclosure can be formulated into high octane fuels, such as AvGas products by admixing with base stocks therefor, and various additives (preferably lead-free additives). In the final, formulated high-octane-number fuel product (e.g., an AvGas product), the concentration of the component produced by the processes of this disclosure can range from, e.g., c1 wt % to c2 wt %, based on the total weight of the fuel product, where c1 and c2 can be, independently, e.g., 5, 6, 8, 10, 15, 20, 25, 30, 35, 40, 45, 50, 55, 60, 65, 70, 75, 80, 85, or 90, as long as c1<c2.

This disclosure can further include one or more of the following aspects and/or embodiments.

Listing of Embodiments

A1. A process for producing a high-octane-number fuel component, the process comprising:
(I) providing a first C8+ hydrocarbon stream comprising p-xylene, o-xylene, m-xylene, and optionally ethylbenzene;
(II) feeding the first C8+ hydrocarbon stream into a C8 splitter to obtain a first o-xylene-rich stream depleted in p-xylene and m-xylene, and a first o-xylene-depleted stream rich in p-xylene and m-xylene;
(III) optionally feeding the first o-xylene-depleted stream to a p-xylene recovery sub-system, from which a p-xylene product stream rich in p-xylene and a raffinate stream depleted in p-xylene are obtained; and
(IV) obtaining the high-octane-number fuel component from one or more of: at least a portion of the first o-xylene-depleted stream; at least a portion of the raffinate stream; and a mixture of at least a portion of the first o-xylene-depleted stream and at least a portion of the raffinate stream.

A2. The process of A1, wherein step (IV) comprises:
(IV-a) abating at least a portion of the ethylbenzene, if any, from at least a portion of one or more of: the first o-xylene-depleted stream; the raffinate stream; and a mixture of the first o-xylene-depleted stream and the raffinate stream, to obtain an ethylbenzene-abated C8 stream; and
(IV-b) providing at least a portion of the ethylbenzene-abated C8 stream as at least a portion of the high-octane-number fuel component.

A3. The process of A2, wherein step (IV-a) comprises one or more of:
(IV-a-1) converting at least a portion of the ethylbenzene into benzene;
(IV-a-2) converting at least a portion of the ethylbenzene into toluene;
(IV-a-3) separating at least a portion of the ethylbenzene using a membrane and/or by distillation; and
(IV-a-4) separating at least a portion of the ethylbenzene using an adsorption chromatography separator.

A4. The process of any of A1 to A3, wherein the first o-xylene-depleted stream comprises o-xylene at a concentration from $c(oX)1$ wt % to $c(oX)2$ wt %, based on the total weight of the first o-xylene-depleted stream, where $c(oX)1$ and $c(oX)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, as long as $c(oX)1<c(oX)2$.

A5. The process of any of A1 to A4, wherein the first o-xylene-depleted stream comprises p-xylene at a concentration from $c(pX)1$ wt % to $c(pX)2$ wt %, m-xylene at a concentration from $c(mX)1$ wt % to $c(mX)2$ wt %, based on the total weight of the first o-xylene-depleted stream, where $c(pX)1$ and $c(pX)2$ can be, independently, e.g., 24, 25, 26, 28, 30, 32, 34, 35, 36, 38, 40, 45, 50, 55, 60, 65, 70, 75, 80, 85, 90, 95, 99, as long as $c(pX)1<c(pX)2$; and $c(mX)1$ and $c(mX)2$ can be, independently, e.g., 50, 52, 54, 55, 56, 58, 60, 62, 64, 65, 66, 68, 70, 75, 80, 85, 90, 95, 96, 97, 98, 99, as long as $c(mX)1<c(mX)2$.

A6. The process of any of A1 to A5, wherein the first o-xylene-depleted stream comprises ethylbenzene at a concentration from $c(EB)1$ wt % to $c(EB)2$ wt %, based on the total weight of the first o-xylene-depleted stream, where $c(EB)1$ and $c(EB)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 11, 12, 13, 14, 15, 16, 17, 18, 19, 20, 21, 22, 23, 24, 25, as long as $c(EB)1<c(EB)2$.

A7. The process of any of A1 to A6, wherein the first o-xylene-depleted stream comprises non-aromatic hydrocarbons at a concentration from $c(nA)1$ wt % to $c(nA)2$ wt %, based on the total weight of the first o-xylene-depleted stream, where $c(nA)1$ and $c(nA)2$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 15, 20, 25, as long as $c(nA)1<c(nA)2$.

A8. The process of A7, wherein the first o-xylene-depleted stream is essentially free of linear paraffins.

A9. The process of any of A1 to A8, wherein the p-xylene recovery subsystem comprises an adsorption chromatographic separation stage, and the raffinate stream comprises p-xylene at a concentration from $c(pX)3$ wt % to $c(pX)4$ wt %, m-xylene at a concentration from $c(mX)3$ wt % to $c(mX)4$ wt %, based on the total weight of the first o-xylene-depleted stream, where $c(pX)3$ and $c(pX)4$ can be, independently, e.g., 0, 0.1, 0.2, 0.4, 0.5, 0.6, 0.8, 1, 2, 3, 4, 5, as long as $c(pX)3<c(pX)4$; and $c(mX)3$ and $c(mX)4$ can be, independently, e.g., 60, 65, 70, 75, 80, 85, 90, 91, 92, 93, 94, 95, as long as $c(mX)3<c(mX)4$.

A10. The process of any of A1 to A8, wherein the p-xylene recovery subsystem comprises a crystallization separation stage, and the raffinate stream comprises p-xylene at a concentration from $c(pX)5$ wt % to $c(pX)6$ wt %, and m-xylene at a concentration from $c(mX)5$ wt % to $c(mX)6$ wt %, based on the total weight of the first o-xylene-depleted stream, where $c(pX)5$ and $c(pX)6$ can be, independently, e.g., 8, 9, 10, 11, 12, 13, 14, 15, 16, 18, 20, 22, 24, 25, 26, 28, 30, 32, 34 as long as $c(pX)5<c(pX)6$; and $c(mX)5$ and $c(mX)6$ can be, independently, e.g., 60, 65, 70, 75, 80, 85, 90, 91, 92, as long as $c(mX)5<c(mX)6$.

A11. The process of any of A1 to A10, further comprising:
(V) feeding at least a portion of the raffinate stream to an isomerization zone operated under isomerization conditions to convert at least a portion of m-xylene in the raffinate stream into p-xylene and/or at least a portion of ethylbenzene, if any, in the raffinate stream into at least one of benzene, toluene, and/or xylenes, to obtain an isomerization effluent stream comprising mixed xylenes; and
(VI) obtaining a second C8+ hydrocarbon stream from the isomerization effluent stream; and
(VII) feeding the second C8+ hydrocarbon stream or a portion thereof to the C8 splitter.

A12. The process of A11, wherein the second C8+ hydrocarbon stream comprises o-xylene at a concentration from $c(oX)3$ wt % to $c(oX)4$ wt %, based on the total weight of the second C8+ hydrocarbon stream, where $c(oX)3$ and $c(oX)4$ can be, independently, e.g., 2, 3, 4, 5, 6, 7, 8, 9, 10, 12, 14, 15, 16, 18, 20, 22, 24, 25, 26, as long as $c(oX)3<c(oX)4$.

A13. The process of A11 or A12, wherein the second C8+ hydrocarbon stream comprises p-xylene at a concentration from $c(pX)7$ wt % to $c(pX)8$ wt %, m-xylene at a concentration from $c(mX)7$ wt % to $c(mX)8$ wt %, based on the total weight of the second C8+ hydrocarbon stream, where $c(pX)7$ and $c(pX)8$ can be, independently, e.g., 5, 6, 7, 8, 9, 10, 12, 14, 15, 16, 18, 20, 22, 24, as long as $c(pX)7<c(pX)8$; and $c(mX)7$ and $c(mX)8$ can be, independently, e.g., 50, 55, 60, 65, 70, 75, 80, 85, 90, 91, 92, 93 as long as $c(mX)7<c(mX)8$.

A14. The process of any of A11 to A13, wherein the second C8+ hydrocarbon stream comprises ethylbenzene at a concentration from $c(EB)3$ wt % to $c(EB)4$ wt %, based on the total weight of the second C8+ hydrocarbon stream, where $c(EB)3$ and $c(EB)4$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 21, as long as $c(EB)3<c(EB)4$.

A15. The process of any of A11 to A14, wherein the second C8+ hydrocarbon stream comprises non-aromatic hydrocarbons at a concentration from $c(nA)3$ wt % to $c(nA)4$ wt %, based on the total weight of the second C8+ hydrocarbon stream, where $c(nA)3$ and $c(nA)4$ can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, as long as $c(nA)3<c(nA)4$.

A16. The process of A15, wherein the second C8+ hydrocarbon stream is essentially free of linear paraffins.

A17. The process of any of A1 to A15, wherein step (I) comprises:
(I-a) feeding a reformer feed stream comprising paraffins and/or naphthenes into a reformer;

(I-b) converting at least a portion of the paraffins and/or naphthenes into aromatic hydrocarbons in the reformer in the presence of a catalyst under reforming conditions to produce a reformer effluent comprising C6, C7, C8, and C9+ aromatic hydrocarbons;

(I-c) obtaining from the reformer effluent a reformate C8+ stream consisting essentially of C8+ hydrocarbons;

(I-d) obtaining at least a portion of the first C8+ hydrocarbon stream from the reformate C8+ stream.

A18. The process of A17, wherein in step (I-b), the reforming conditions comprise a temperature from 427 to 565° C. (from 800 to 1050° F.), a liquid hourly space velocity ("LHSV") from 0.3 to 3.0 hour', and/or a pressure from 241 to 3,447 kilopascal (gauge) (from 35 to 500 psig).

A19. The process of A17 or A18, wherein the reformate C8+ stream is essentially free of linear paraffins.

A20. The process of any of A17 to A19, wherein in the reformate C8+ stream comprises ethylbenzene at a concentration from c(EB)5 wt % to c(EB)6 wt %, based on the total weight of the reformate C8+ stream, where c(EB)5 and c(EB)5 can be, independently, e.g., 0, 0.02, 0.04, 0.05, 0.06, 0.08, 0.1, 0.2, 0.4, 0.5, 0.6, 0.8, 1, 2, 3, 4, 5, 6, 8, 10, 12, 14, 15, 16, 18, 20, 22, 24, 25, 26, 28, 30 as long as c(EB)5<c(EB)6.

A21. The process of A20, wherein c(EB)5≥5 wt %, and step (I-d) comprises:

(I-d-1) removing at least a portion of the ethylbenzene in the reformate C8+ stream to obtain a third C8+ stream having a reduced ethylbenzene concentration compared to the reformate C8+ stream; and (I-d-2) providing at least a portion of the third C8+ stream as the at least a portion of the first C8+ hydrocarbon stream.

A22. The process of A21, wherein step (I-d-1) comprises distilling the reformate C8+ stream and/or extracting the reformate C8+ stream using an extraction solvent to remove the at least a portion of the ethylbenzene in the reformate C8+ stream.

A23. The process of A21, wherein step (I-d-1) comprises:

(I-d-1-a) feeding at least a portion of the reformate C8+ stream into a first ethylbenzene conversion zone;

(I-d-1-b) converting at least a portion of the ethylbenzene in the reformate C8+ stream in the first ethylbenzene conversion zone in the presence of a first ethylbenzene conversion catalyst into benzene to obtain a first ethylbenzene conversion zone effluent; and (I-d-1-c) obtaining the third C8+ stream from the first ethylbenzene conversion effluent consisting essentially of xylenes and having an ethylbenzene concentration lower than c(EB)5.

A24. The process of any of A17 to A23, wherein step (I-c) comprises:

(I-c-1) obtaining a C6+ hydrocarbon stream from the reformer effluent;

(I-c-2) feeding at least a portion of the C6+ hydrocarbon stream into a second ethylbenzene conversion zone;

(I-c-3) converting at least a portion of the ethylbenzene in the C6+ hydrocarbon stream in the second conversion zone in the presence of a second ethylbenzene conversion catalyst to into benzene to obtain a second ethylbenzene conversion zone effluent; and (I-c-4) obtaining the reformate C8+ stream from the second ethylbenzene conversion zone effluent.

A25. The process of any of A1 to A24, wherein step (I) comprises:

(I-e) feeding a C9+ aromatic hydrocarbon stream and a C6-C7 aromatic hydrocarbon stream into a transalkylation zone;

(I-f) converting at least a portion of the C9+ aromatic hydrocarbons and C6-C7 aromatic hydrocarbons under transalkylation conditions in the transalkylation zone to produce a transalkylation effluent comprising C6, C7, C8, and C9+ aromatic hydrocarbons;

(I-g) obtaining from the transalkylation effluent a transalkylation C8+ stream consisting essentially of C8+ hydrocarbons; and (I-h) obtaining at least a portion of the first C8+ hydrocarbon stream from the transalkyaltion C8+ stream.

A26. The process of any of A1 to A25, wherein step (I) comprises:

(I-i) feeding toluene into a first toluene disproportionation zone;

(I-j) converting at least a portion of the toluene in step (I-i) in the presence of a disproportionation catalyst under disproportionation conditions to produce a first disproportionation effluent comprising C7, C8, and C9+ aromatic hydrocarbons;

(I-k) obtaining from the first disproportionation effluent a first disproportionation C8+ stream consisting essentially of C8+ aromatic hydrocarbons; and (I-1) obtaining at least a portion of the first C8+ hydrocarbon stream from the first disproportionation C8+ stream.

A27. The process of any of A1 to A26, the process further comprising:

(I-m) feeding C6-C7 aromatic hydrocarbons and a methylating agent into a first methylation zone;

(I-n) reacting the C6-C7 aromatic hydrocarbons with the methylating agent in the first methylation zone in the presence of a first methylation catalyst under first methylation conditions to produce a first methylation effluent comprising C7 and C8+ aromatic hydrocarbons;

(I-o) obtaining from the first methylation effluent a first methylation C8+ stream consisting essentially of C8+ aromatic hydrocarbons; and (I-p) obtaining at least a portion of the first C8+ hydrocarbon stream from the first methylation C8+ stream.

A28. The process of any of A1 to A27, wherein step (I) comprises:

(I-q) providing a precursor C8+ hydrocarbon stream comprising non-aromatic hydrocarbons; and (I-r) removing at least a portion of the non-aromatic hydrocarbons from the precursor C8+ hydrocarbon stream to obtain at least a portion of the first C8+ hydrocarbon stream.

A29. The process of any of A1 to A28, the process further comprising:

(VIII) feeding toluene into a second toluene disproportionation zone;

(IX) converting at least a portion of the toluene in step (VIII) in the presence of a shape selective catalyst to produce a second disproportionation effluent comprising C7, C8, and C9+ aromatic hydrocarbons;

(X) obtaining from the second disproportionation effluent a second disproportionation C8+ stream consisting essentially of C8+ aromatic hydrocarbons having a p-xylene concentration of at least 25 wt %, based on the total weight of the second disproportionation C8+ stream; and (XI) feeding at least a portion of the second disproportionation C8+ stream to the p-xylene recovery subsystem of step (III).

A30. The process of A29, wherein in step (X), the second disproportionation C8+ stream comprises o-xylene at a concentration from c(oX)5 wt % to c(oX)6 wt %, based on the total weight of the second disproportionation C8+ stream, wherein c(oX)5 and c(oX)6 can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, 26, as long as c(oX)5<c(oX)6.

A31. The process of A29 or A30, wherein in step (X), the second disproportionation C8+ stream comprises p-xylene at a concentration from c(pX)9 wt % to c(pX)10 wt %, based on the total weight of the second disproportionation C8+ stream, wherein c(pX)9 and c(pX)10 can be, independently, e.g., 25, 26, 28, 30, 35, 40, 45, 50, 55, 60, 65, 70, 75, 80, 85, 90, 95, 96, 97, as long as c(pX)9<c(pX)10.

A32. The process of any of A1 to A31, wherein in step (X), the second disproportionation C8+ stream comprises ethylbenzene at a concentration from c(EB)9 wt % to c(EB)10 wt %, based on the total weight of the second disproportionation C8+ stream, wherein c(EB)9 and c(EB)10 can be, independently, e.g., 0, 0.02, 0.04, 0.05, 0.06, 0.08, 0.1, 0.2, 0.4, 0.5, 0.6, 0.8, 1, 2, 3, 4, 5, as long as c(EB)9<c(EB)10.

A33. The process of any of A1 to A32, wherein in step (X), the second disproportionation C8+ stream comprises non-aromatic hydrocarbons at a total concentration from c(nA)9 wt % to c(nA)10 wt %, based on the total weight of the second disproportionation C8+ stream, wherein c(nA)9 and c(nA)10 can be, independently, e.g., 0, 0.02, 0.04, 0.05, 0.06, 0.08, 0.1, 0.2, 0.4, 0.5, 0.6, 0.8, 1, 2, 3, 4, 5, as long as c(nA)9<c(nA)10.

A33a. The process of any of A1 to A33, wherein in step (X), the second disproportionation C8+ stream exhibits a m-xylene/o-xylene molar ratio in a range from r1 to r2, wherein r1 and r2 can be, independently, 2, 3, 4, 5, 6, 7, 8, 9, 10, 11, 12, 13, 14, 15, 16, 17, 18, 19, 20, as long as r1<r2; preferably r1≥5, more preferably r1≥8.

A34. The process of any of A1 to A33, the process further comprising:
(XII) feeding C6-C7 aromatic hydrocarbon(s) and a methylating agent into a second methylation zone;
(XIII) reacting the C6-C7 aromatic hydrocarbons with the methylating agent in the second methylation zone in the presence of a second methylation catalyst under second methylation conditions to produce a second methylation effluent comprising C7 and C8+ aromatic hydrocarbons;
(XIV) obtaining from the second methylation effluent a methylation C8+ stream consisting essentially of C8+ aromatic hydrocarbons having a p-xylene concentration of at least 25 wt %, based on the total weight of the second methylation C8+ stream; and
(XV) feeding at least a portion of the second methylation C8+ stream to the p-xylene recovery sub-system of step (III).

A35. The process of A34, wherein in step (XII), the second methylation C8+ stream has at least one of the following features:
(a) an o-xylene concentration from c(oX)1 wt % to c(oX)2 wt %, based on the total weight of the second methylation C8+ stream, wherein c(oX)1 and c(oX)2 can be, independently, e.g., 0, 0.02, 0.04, 0.01, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, 26 as long as c(oX)1<c(oX)2;
(b) an m-xylene concentration from c(mX)1 wt % to c(mX)2 wt %, based on the total weight of the second methylation C8+ stream, wherein c(mX)1 and c(mX)2 can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, 26 as long as c(mX)1<c(mX)2;
(c) a p-xylene concentration from c(pX)1 wt % to c(pX)2 wt %, based on the total weight of the second methylation C8+ stream, wherein c(pX)1 and c(pX)2 can be, independently, e.g., 25, 30, 35, 40, 45, 50, 55, 60, 65, 70, 75, 80, 85, 90, 91, 92, 93, 94, 95, as long as c(pX)1<c(pX)2;
(d) an m-xylene/o-xylene ratio from r(m/o)1 to r(m/o)2, where r(m/o)1 and r(m/o)2 can be, independently, e.g., 2.1, 2.5, 3.0, 3.5, 4.0, 4.5, 5.0, 6.0, 7.0, 7.5, 8.0, 9.0, 10, 11, 12, 12.5, 13, 14, 15, 16, 17, 17.5, 18, 19, 20, as long as r(m/o)1<r(m/o)2;
(e) an ethylbenzene concentration from c(EB)1 wt % to c(EB)2 wt %, based on the total weight of the second methylation C8+ stream, wherein c(EB)2 and c(EB)2 can be, independently, e.g., 0, 0.02, 0.04, 0.05, 0.06, 0.08, 0.1, 0.2, 0.4, 0.5, 0.6, 0.8, 1, 2, 3, 4, 5, as long as c(EB)1<c(EB)2; and
(f) a non-aromatic hydrocarbons concentration from c(nA)1 wt % to c(nA)2 wt %, based on the total weight of the second methylation C8+ stream, wherein c(nA)1 and c(nA)8 can be, independently, e.g., 0, 0.02, 0.04, 0.05, 0.06, 0.08, 0.1, 0.2, 0.4, 0.5, 0.6, 0.8, 1, 2, 3, 4, 5, as long as c(nA)1<c(nA)2.

A36. The process of any of A1 to A35, wherein the first C8+ hydrocarbon stream comprises C9+ hydrocarbons, the first o-xylene-rich stream comprises C9+ hydrocarbons, and the process further comprises:
(XVI) separating the first o-xylene-rich stream to obtain an o-xylene product stream and a C9+ hydrocarbon stream; and
(XVII) obtaining at least a portion of the high-octane-number fuel component from at least a portion of the C9+ hydrocarbon stream.

A37. The process of any of A1 to A36, wherein the high-octane-number fuel component has one or more of the following features:
(a) an o-xylene concentration from c(oX)7 wt % to c(oX)8 wt %, based on the total weight of the high-octane-number fuel component, wherein c(oX)7 and c(oX)8 can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, as long as c(oX)7<c(oX)8;
(b) a p-xylene concentration from c(pX)11 wt % to c(pX)12 wt %, based on the total weight of the high-octane-number fuel component, wherein c(pX)11 and c(pX)12 can be, independently, e.g., 0, 0.1, 0.2, 0.4, 0.5, 0.6, 0.8, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 99, 100, as long as c(pX)11<c(pX)12;
(c) an m-xylene concentration from c(mX)11 wt % to c(mX)12 wt %, based on the total weight of the high octane number fuel component, wherein c(mX)11 and c(mX)12 can be, independently, e.g., 0, 0.1, 0.2, 0.4, 0.5, 0.6, 0.8, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 99, 100, as long as c(mX)11<c(mX)12; and (d) an ethylbenzene concentration from c(EB)7 wt % to c(EB)8 wt %, based on the total weight of the high-octane-number fuel component, wherein c(EB)7 and c(EB)8 can be, independently, e.g., 0, 0.02, 0.04, 0.05, 0.06, 0.08, 0.1, 0.2, 0.4, 0.5, 0.6, 0.8, 1, 2, 3, 4, 56, 7, 8, 9, 10, 11, 12, 13, 14, 15, 16, 17, 18, 19, 20, 21, 22, 23, 24, 25, as long as c(EB)11<c(EB)12; and (e) an octane number 95, preferably 96, preferably 97, preferably 98, preferably 99, preferably 100, preferably 101, preferably 102, still more preferably 103, as determined by ASTM D2700.

A38. The process of any of A1 to A37, wherein the xylene splitter comprises one or more of a distillation column, a membrane separator, and an adsorption chromatographic separator.

B1. A process for producing a high-octane-number aviation gasoline blend component, the process comprising:
(A) feeding toluene into a toluene disproportionation zone;
(B) converting at least a portion of the toluene in the presence of a shape selective catalyst to produce a disproportionation effluent comprising C7, C8, and C9+ aromatic hydrocarbons;
(C) obtaining from the disproportionation effluent a disproportionation C8+ stream consisting essentially of C8+ aromatic hydrocarbons having a p-xylene concentration of at least 50 wt %, based on the total weight of the second disproportionation C8+ stream;
(D) feeding at least a portion of the disproportionation C8+ stream to a p-xylene recovery sub-system, from which a p-xylene product stream rich in p-xylene and a raffinate stream depleted in p-xylene are obtained; and
(E) obtaining at least a portion of the high-octane-number fuel component from the raffinate stream.

B2. The process of B1, wherein the disproportionation C8+ stream comprises o-xylene at a concentration from c(oX)1 wt % to c(oX)2 wt %, based on the total weight of the first o-xylene-depleted stream, where c(oX)1 and c(oX)2 can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, 26, as long as c(oX)1<c(oX)2.

B3. The process of B1 or B2, wherein the disproportionation C8+ stream comprises ethylbenzene at a concentration from c(EB)1 wt % to c(EB)2 wt %, based on the total weight of the first o-xylene-depleted stream, where c(EB)1 and c(EB)2 can be, independently, e.g., 0, 0.02, 0.04, 0.05, 0.06, 0.08, 0.1, 0.2, 0.4, 0.5, 0.6, 0.8, 1, 2, 3, 4, 5, as long as c(EB)1<c(EB)2.

B4. The process of any of B1 to B3, wherein the disproportionation C8+ stream comprises p-xylene at a concentration from c(pX)1 wt % to c(pX)2 wt %, based on the total weight of the second disproportionation C8+ stream, wherein c(pX)1 and c(pX)2 can be, independently, e.g., 25, 26, 28, 30, 35, 40, 45, 50, 55, 60, 65, 70, 75, 80, 85, 90, 95, 96, 97, as long as c(pX)9<c(pX)10.

B5. The process of any of B1 to B4, wherein the disproportionation C8+ stream comprises non-aromatic hydrocarbons at a concentration from c(nA)1 wt % to c(nA)2 wt %, based on the total weight of the first o-xylene-depleted stream, where c(nA)1 and c(nA)2 can be, independently, e.g., 0, 0.02, 0.04, 0.05, 0.06, 0.08, 0.1, 0.2, 0.4, 0.5, 0.6, 0.8, 1, 2, 3, 4, 5, as long as c(nA)1<c(nA)2.

B6. The process of any of B1 to B5, the process further comprising:
(F) providing a first C8+ hydrocarbon stream comprising p-xylene, o-xylene, m-xylene, and optionally ethylbenzene;
(G) feeding the first C8+ hydrocarbon stream into a C8 splitter to obtain a first o-xylene-rich stream depleted in p-xylene and m-xylene, and a first o-xylene-depleted stream rich in p-xylene and m-xylene;
(H) option feeding the first o-xylene-depleted stream to the p-xylene recovery sub-system of step (D), from which a p-xylene product stream rich in p-xylene and a raffinate stream depleted in p-xylene are obtained; and
(I) obtaining at least a portion of the high-octane-number fuel component from one or more of: the first o-xylene-depleted stream; the raffinate stream; and a mixture of the first o-xylene-depleted stream and the raffinate stream.

B7. The process of any of B1 to B6, the process further comprising any of the other process steps and/or features recited in A2 to A38.

C1. A process for producing a high-octane-number aviation gasoline blend component, the process comprising:
(a) feeding C6-C7 aromatic hydrocarbon(s) and a methylating agent into a methylation zone;
(b) reacting the C6-C7 aromatic hydrocarbons with the methylating agent in the methylation zone in the presence of a methylation catalyst under methylation conditions to produce a methylation effluent comprising C7 and C8+ aromatic hydrocarbons;
(c) obtaining from the methylation effluent a methylation C8+ stream consisting essentially of C8+ aromatic hydrocarbons having a p-xylene concentration of at least 25 wt %, based on the total weight of the methylation C8+ stream;
(d) feeding at least a portion of the methylation C8+ stream to a p-xylene recovery sub-system, from which a p-xylene product stream rich in p-xylene and a raffinate stream depleted in p-xylene are obtained; and
(e) obtaining at least a portion of the high-octane-number fuel component from the raffinate stream.

C2. The process of C1, wherein the methylation C8+ stream comprises o-xylene at a concentration from c(oX)1 wt % to c(oX)2 wt %, based on the total weight of the first o-xylene-depleted stream, where c(oX)1 and c(oX)2 can be, independently, e.g., 0, 0.02, 0.04, 0.01, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, 26, as long as c(oX)1<c(oX)2.

C3. The process of C1 or C2, wherein the methylation C8+ stream comprises p-xylene at a concentration from c(pX)1 wt % to c(pX)2 wt %, based on the total weight of the second methylation C8+ stream, wherein c(pX)1 and c(pX)2 can be, independently, e.g., 25, 30, 35, 40, 45, 50, 55, 60, 65, 70, 75, 80, 85, 90, 91, 92, 93, 94, 95, as long as c(pX)1<c(pX)2.

C4. The process of any of C1 to C3, wherein the methylation C8+ stream comprises an m-xylene at concentration from c(mX)1 wt % to c(mX)2 wt %, based on the total weight of the second methylation C8+ stream, wherein c(mX)1 and c(mX)2 can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, 26, as long as c(mX)1<c(mX)2.

C5. The process of any of C1 to C4, wherein the methylation C8+ stream has an m-xylene/o-xylene ratio from r(m/o)1 to r(m/o)2, where r(m/o)1 and r(m/o)2 can be, independently, e.g., 2.1, 2.5, 3.0, 3.5, 4.0, 4.5, 5.0, 6.0, 7.0, 7.5, 8.0, 9.0, 10, 11, 12, 12.5, 13, 14, 15, 16, 17, 17.5, 18, 19, 20, as long as r(m/o)1<r(m/o)2.

C6. The process of any of C1 to C5, wherein the methylation C8+ stream comprises ethylbenzene at a concentration from c(EB)1 wt % to c(EB)2 wt %, based on the total weight of the first o-xylene-depleted stream, where c(EB)1 and c(EB)2 can be, independently, e.g., 0, 0.02, 0.04, 0.05, 0.06, 0.08, 0.1, 0.2, 0.4, 0.5, 0.6, 0.8, 1, 2, 3, 4, 5, as long as c(EB)1<c(EB)2.

C7. The process of any of C1 to C6, wherein the methylation C8+ stream comprises non-aromatic hydrocarbons at a concentration from c(nA)1 wt % to c(nA)2 wt %, based on the total weight of the first o-xylene-depleted stream, where c(nA)1 and c(nA)2 can be, independently, e.g., 0, 0.02, 0.04, 0.05, 0.06, 0.08, 0.1, 0.2, 0.4, 0.5, 0.6, 0.8, 1, 2, 3, 4, 5, as long as c(nA)1<c(nA)2.

C8. The process of any of C1 to C7, the process further comprising:
(f) providing a first C8+ hydrocarbon stream comprising p-xylene, o-xylene, m-xylene, and optionally ethylbenzene;
(g) feeding the first C8+ hydrocarbon stream into a C8 splitter to obtain a first o-xylene-rich stream depleted in p-xylene and m-xylene, and a first o-xylene-depleted stream rich in p-xylene and m-xylene;
(h) option feeding the first o-xylene-depleted stream to the p-xylene recovery sub-system of step (D), from which a p-xylene product stream rich in p-xylene and a raffinate stream depleted in p-xylene are obtained; and
(i) obtaining at least a portion of the high-octane-number fuel component from one or more of: the first o-xylene-depleted stream; the raffinate stream; and a mixture of the first o-xylene-depleted stream and the raffinate stream.

C9. The process of any of C1 to C9, the process further comprising any of the other process steps and/or features recited in A2 to A38.

D1. A process for producing a high-octane-number fuel component, the process comprising:
(1) providing a C8 aromatic hydrocarbon stream comprising p-xylene, o-xylene, m-xylene, and optionally ethylbenzene;
(2) feeding the C8 aromatic hydrocarbon stream to a p-xylene recovery sub-system, from which a p-xylene product stream rich in p-xylene and a raffinate stream depleted in p-xylene are obtained; and
(3) obtaining the high-octane-number fuel component from one or more of: at least a portion of the C8 aromatic hydrocarbon stream; at least a portion of the raffinate stream; and a mixture of at least a portion of the C8 aromatic hydrocarbon stream and at least a portion of the raffinate stream.

D2. The process of D1, further comprising:
(4) feeding at least a portion of the raffinate stream to an isomerization zone operated under isomerization conditions to convert at least a portion of m-xylene in the raffinate stream into p-xylene and/or at least a portion of ethylbenzene, if any, in the raffinate stream into at least one of benzene, toluene, and/or xylenes, to obtain an isomerization effluent stream comprising mixed xylenes; and
(5) obtaining at least a portion of the C8 aromatic hydrocarbon stream from the isomerization effluent stream.

D3. The process of D1 or D2, wherein step (1) comprises:
(1a) providing a first C8+ hydrocarbon stream comprising p-xylene, o-xylene, m-xylene, and optionally ethylbenzene;
(1b) feeding the first C8+ hydrocarbon stream into a C8 splitter to obtain a first o-xylene-rich stream depleted in p-xylene and m-xylene, and a first o-xylene-depleted stream rich in p-xylene and m-xylene; and
(1c) providing at least a portion of the first o-xylene-depleted stream as at least a portion of the C8 aromatic hydrocarbon stream.

D4. The process of D1 to D3, further comprising any of the other process steps and/or features recited in A2 to A38.

D5. The process of any of D1 to D4, wherein the C8 aromatic hydrocarbon stream comprises o-xylene at a concentration from c(oX)1 wt % to c(oX)2 wt %, based on the total weight of the first o-xylene-depleted stream, where c(oX)1 and c(oX)2 can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 12, 14, 15, 16, 18, 20, 22, 24, 25, as long as c(oX)1<c(oX)2.

D6. The process of any of D1 to D5, wherein the C8 aromatic hydrocarbon stream comprises p-xylene at a concentration from c(pX)1 wt % to c(pX)2 wt %, m-xylene at a concentration from c(mX)1 wt % to c(mX)2 wt %, based on the total weight of the first o-xylene-depleted stream, where c(pX)1 and c(pX)2 can be, independently, e.g., 24, 25, 26, 28, 30, 32, 34, 35, 36, 38, 40, 45, 50, 55, 60, 65, 70, 75, 80, 85, 90, 95, 99, as long as c(pX)1<c(pX)2; and c(mX)1 and c(mX)2 can be, independently, e.g., 50, 52, 54, 55, 56, 58, 60, 62, 64, 65, 66, 68, 70, 75, 80, 85, 90, 95, 96, 97, 98, 99, as long as c(mX)1<c(mX)2.

D7. The process of any of D1 to D6, wherein the C8 aromatic hydrocarbon stream comprises ethylbenzene at a concentration from c(EB)1 wt % to c(EB)2 wt %, based on the total weight of the first o-xylene-depleted stream, where c(EB)1 and c(EB)2 can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 11, 12, 13, 14, 15, 16, 17, 18, 19, 20, 21, 22, 23, 24, 25, as long as c(EB)1<c(EB)2.

D8. The process of any of D1 to D7, wherein the C8 aromatic hydrocarbon stream comprises non-aromatic hydrocarbons at a concentration from c(nA)1 wt % to c(nA)2 wt %, based on the total weight of the first o-xylene-depleted stream, where c(nA)1 and c(nA)2 can be, independently, e.g., 0, 0.02, 0.04, 0.05, 0.06, 0.08, 0.1, 0.2, 0.4, 0.5, 0.6, 0.8, 1, 2, 3, 4, 5, 6, 7, 8, 9, 10, 15, 20, 25, as long as c(nA)1<c(nA)2.

D9. The process of D8, wherein the C8 aromatic hydrocarbon stream is essentially free of linear paraffins.

What is claimed is:

1. A process for producing a high-octane-number fuel component, the process comprising:
(I) providing a first C8+ hydrocarbon stream comprising p-xylene, o-xylene, m-xylene, and ethylbenzene;
(II) feeding the first C8+ hydrocarbon stream into a C8 splitter to obtain a first o-xylene-rich stream depleted in p-xylene and m-xylene, and a first o-xylene-depleted stream rich in p-xylene and m-xylene;
(III) feeding the first o-xylene-depleted stream to a p-xylene recovery sub-system, from which a p-xylene product stream rich in p-xylene and a raffinate stream depleted in p-xylene are obtained;
(IV) obtaining the high-octane-number fuel component from one or more of: at least a portion of the first o-xylene-depleted stream; at least a portion of the raffinate stream; and a mixture of at least a portion of the first o-xylene-depleted stream and at least a portion of the raffinate stream; and (IV-a) abating at least a portion of the ethylbenzene from the high-octane-number fuel component comprising at least the portion of the first o-xylene-depleted stream, the raffinate stream, a mixture of the first o-xylene-depleted stream and the raffinate stream, or a combination thereof, to obtain an ethylbenzene-abated C8 stream.

2. The process of claim 1, wherein step (IV) comprises:
(IV-b) providing at least a portion of the ethylbenzene-abated C8 stream as at least a portion of the high-octane-number fuel component.

3. The process of claim 1, wherein step (IV-a) comprises one or more of:
(IV-a-1) converting at least a portion of the ethylbenzene into benzene;
(IV-a-2) converting at least a portion of the ethylbenzene into toluene;
(IV-a-3) separating at least a portion of the ethylbenzene using a membrane and/or by distillation; and
(IV-a-4) separating at least a portion of the ethylbenzene using an adsorption chromatography separator.

4. The process of claim 1, wherein the first o-xylene-depleted stream has at least one of the following features:
(a) an o-xylene concentration from 0 to 25 wt %, based on the total weight of the first o-xylene-depleted stream;
(b) a p-xylene concentration from 24 wt % to 99 wt %, m-xylene at a concentration from 50 wt % to 99 wt %, based on the total weight of the first o-xylene-depleted stream;
(c) an ethylbenzene concentration from 0 to 25 wt %, based on the total weight of the first o-xylene-depleted stream; and
(d) a total non-aromatic hydrocarbons concentration from 0 to 25 wt %, based on the total weight of the first o-xylene-depleted stream.

5. The process of claim 1, wherein the p-xylene recovery sub-system comprises an adsorption chromatographic separation stage, and the raffinate stream comprises p-xylene at a concentration from 0 to 5 wt %, and m-xylene at a concentration from 60 wt % to 95 wt %, based on the total weight of the first o-xylene-depleted stream.

6. The process of claim 1, wherein the p-xylene recovery sub-system comprises a crystallization separation stage, and the raffinate stream comprises p-xylene at a concentration from 8 wt % to 34 wt %, and m-xylene at a concentration from 60 wt % to 92 wt %, based on the total weight of the first o-xylene-depleted stream.

7. The process of claim 1, further comprising:
(V) feeding at least a portion of the raffinate stream to an isomerization zone operated under isomerization conditions to convert at least a portion of m-xylene in the raffinate stream into p-xylene and/or at least a portion of the ethylbenzene, if any, in the raffinate stream into at least one of benzene, toluene, and/or xylenes, to obtain an isomerization effluent stream comprising mixed xylenes; and
(VI) obtaining a second C8+ hydrocarbon stream from the isomerization effluent stream; and
(VII) feeding the second C8+ hydrocarbon stream or a portion thereof to the C8 splitter.

8. The process of claim 1, wherein step (I) comprises:
(I-a) feeding a reformer feed stream comprising paraffins and/or naphthenes into a reformer;
(I-b) converting at least a portion of the paraffins and/or naphthenes into aromatic hydrocarbons in the reformer in the presence of a catalyst under reforming conditions to produce a reformer effluent comprising C6, C7, C8, and C9+ aromatic hydrocarbons;
(I-c) obtaining from the reformer effluent a reformate C8+ stream consisting essentially of C8+ hydrocarbons; and
(I-d) obtaining at least a portion of the first C8+ hydrocarbon stream from the reformate C8+ stream.

9. The process of claim 8, wherein in step (I-b), the reforming conditions comprise a temperature from 427 to 565° C. (from 800 to 1050° F.), a liquid hourly space velocity ("LHSV") from 0.3 to 3.0 hour$^{-1}$, and/or a pressure from 241 to 3,447 kilopascal (gauge) (from 35 to 500 psig).

10. The process of claim 8, wherein in step (I-c), the reformate C8+ stream comprises ethylbenzene at a concentration from 0 to 30 wt %, based on the total weight of the reformate C8+ stream.

11. The process of claim 10, wherein c(EB)5≥5 wt %, and step (I-d) comprises:
(I-d-1) removing at least a portion of the ethylbenzene in the reformate C8+ stream to obtain a third C8+ stream having a reduced ethylbenzene concentration compared to the reformate C8+ stream; and
(I-d-2) providing at least a portion of the third C8+ stream as the at least a portion of the first C8+ hydrocarbon stream.

12. The process of claim 11, wherein step (I-d-1) comprises distilling the reformate C8+ stream and/or extracting the reformate C8+ stream using an extraction solvent to remove the at least a portion of the ethylbenzene in the reformate C8+ stream.

13. The process of claim 11, wherein step (I-d-1) comprises:
(I-d-1-a) feeding at least a portion of the reformate C8+ stream into a first ethylbenzene conversion zone;
(I-d-1-b) converting at least a portion of the ethylbenzene in the reformate C8+ stream in the first ethylbenzene conversion zone in the presence of a first ethylbenzene conversion catalyst to convert at least a portion of the ethylbenzene into benzene to obtain a first ethylbenzene conversion zone effluent; and
(I-d-1-c) obtaining the third C8+ stream from the first ethylbenzene conversion effluent consisting essentially of xylenes and having an ethylbenzene concentration lower than c(EB)5.

14. The process of claim 8, wherein step (I-c) comprises:
(I-c-1) obtaining a C6+ hydrocarbon stream from the reformer effluent;
(I-c-2) feeding at least a portion of the C6+ hydrocarbon stream into a second ethylbenzene conversion zone;
(I-c-3) converting at least a portion of the ethylbenzene in the C6+ hydrocarbon stream in the second conversion zone in the presence of a second ethylbenzene conversion catalyst to convert at least a portion of the ethylbenzene into benzene to obtain a second ethylbenzene conversion zone effluent; and
(I-c-4) obtaining the reformate C8+ stream from the second ethylbenzene conversion zone effluent.

15. The process of claim 1, wherein step (I) comprises:
(I-e) feeding a C9+ aromatic hydrocarbon stream and a C6-C7 aromatic hydrocarbon stream into a transalkylation zone;
(I-f) converting at least a portion of the C9+ aromatic hydrocarbons and C6-C7 aromatic hydrocarbons under transalkylation conditions in the transalkylation zone to produce a transalkylation effluent comprising C6, C7, C8, and C9+ aromatic hydrocarbons;

(I-g) obtaining from the transalkylation effluent a transalkylation C8+ stream consisting essentially of C8+ hydrocarbons; and (I-h) obtaining at least a portion of the first C8+ hydrocarbon stream from the transalkyaltion C8+ stream.

16. The process of claim 1, wherein step (I) comprises:

(I-i) feeding toluene into a first toluene disproportionation zone;

(I-j) converting at least a portion of the toluene in step (I-i) in the presence of a disproportionation catalyst under disproportionation conditions to produce a first disproportionation effluent comprising C7, C8, and C9+ aromatic hydrocarbons;

(I-k) obtaining from the first disproportionation effluent a first disproportionation C8+ stream consisting essentially of C8+ aromatic hydrocarbons; and (I-l) obtaining at least a portion of the first C8+ hydrocarbon stream from the first disproportionation C8+ stream.

17. The process of claim 1, the process further comprising:

(I-m) feeding C6-C7 aromatic hydrocarbons and a methylating agent into a first methylation zone;

(I-n) reacting the C6-C7 aromatic hydrocarbons with the methylating agent in the first methylation zone in the presence of a first methylation catalyst under first methylation conditions to produce a first methylation effluent comprising C7 and C8+ aromatic hydrocarbons;

(I-o) obtaining from the first methylation effluent a first methylation C8+ stream consisting essentially of C8+ aromatic hydrocarbons; and (I-p) obtaining at least a portion of the first C8+ hydrocarbon stream from the first methylation C8+ stream.

18. The process of claim 1, wherein step (I) comprises:

(I-q) providing a precursor C8+ hydrocarbon stream comprising non-aromatic hydrocarbons; and (I-r) removing at least a portion of the non-aromatic hydrocarbons from the precursor C8+ hydrocarbon stream to obtain at least a portion of the first C8+ hydrocarbon stream.

19. The process of claim 1, the process further comprising:

(VIII) feeding toluene into a second toluene disproportionation zone;

(IX) converting at least a portion of the toluene in step (VIII) in the presence of a shape selective catalyst to produce a second disproportionation effluent comprising C7, C8, and C9+ aromatic hydrocarbons;

(X) obtaining from the second disproportionation effluent a second disproportionation C8+ stream consisting essentially of C8+ aromatic hydrocarbons having a p-xylene concentration of at least 25 wt %, based on the total weight of the second disproportionation C8+ stream; and (XI) feeding at least a portion of the second disproportionation C8+ stream to the p-xylene recovery sub-system of step (III).

20. The process of claim 19, wherein in step (X), the second disproportionation C8+ stream has at least one of the following features:

(a) an o-xylene concentration from 0 to 26 wt %, based on the total weight of the second disproportionation C8+ stream;

(b) a p-xylene concentration from 25 wt % to 97 wt %, based on the total weight of the second disproportionation C8+ stream;

(c) an ethylbenzene concentration from 0 to 5 wt %, based on the total weight of the second disproportionation C8+ stream;

(d) a total non-aromatic hydrocarbons concentration from 0 to 5 wt %, based on the total weight of the second disproportionation C8+ stream; and (e) a m-xylene/o-xylene molar ratio in a range from 2 to 20.

21. The process of claim 1, further comprising:

(XII) feeding C6-C7 aromatic hydrocarbon(s) and a methylating agent into a second methylation zone;

(XIII) reacting the C6-C7 aromatic hydrocarbons with the methylating agent in the second methylation zone in the presence of a second methylation catalyst under second methylation conditions to produce a second methylation effluent comprising C7 and C8+ aromatic hydrocarbons;

(XIV) obtaining from the second methylation effluent a methylation C8+ stream consisting essentially of C8+ aromatic hydrocarbons having a p-xylene concentration of at least 25 wt %, based on the total weight of the second methylation C8+ stream; and (XV) feeding at least a portion of the second methylation C8+ stream to the p-xylene recovery sub-system of step (III).

22. The process of claim 21, wherein in step (XII), the second methylation C8+ stream has at least one of the following features:

(a) an o-xylene concentration from 0 to 26 wt %, based on the total weight of the second methylation C8+ stream;

(b) an m-xylene concentration from 0 to 26 wt %, based on the total weight of the second methylation C8+ stream;

(c) a p-xylene concentration from 25 wt % to 95 wt %, based on the total weight of the second methylation C8+ stream;

(d) an m-xylene/o-xylene ratio from 2.1 to 20;

(e) an ethylbenzene concentration from 0 to 5 wt %, based on the total weight of the second methylation C8+ stream; and (f) a non-aromatic hydrocarbons concentration from 0 to 5 wt %, based on the total weight of the second methylation C8+ stream.

23. The process of claim 1, wherein the first C8+ hydrocarbon stream comprises C9+ hydrocarbons, the first o-xylene-rich stream comprises C9+ hydrocarbons, and the process further comprises:

(XVI) separating the first o-xylene-rich stream to obtain an o-xylene product stream and a C9+ hydrocarbon stream; and (XVII) obtaining at least a portion of the high-octane-number fuel component from at least a portion of the C9+ hydrocarbon stream.

24. The process of claim 1, wherein the high-octane-number fuel component has one or more of the following features:

(a) an o-xylene concentration from 0 to 25 wt %, based on the total weight of the high-octane-number fuel component;

(b) a p-xylene concentration from 0 to 100 wt %, based on the total weight of the high-octane-number fuel component;

(c) an m-xylene concentration from 0 to 100 wt %, based on the total weight of the high octane number fuel component; and (d) an ethylbenzene concentration from 0 to 25 wt %, based on the total weight of the high-octane-number fuel component; and
(e) an octane number ≥95, as determined by ASTM D2700.

\* \* \* \* \*